United States Patent [19]

Lang

[11] Patent Number: 4,794,109
[45] Date of Patent: Dec. 27, 1988

[54] 6-HYDROXY-LOWER ALKYLPENEM COMPOUNDS, PHARMACEUTICAL PREPARATIONS THAT CONTAIN THESE COMPOUNDS, AND THE USE OF THE LATTER

[75] Inventor: Erfinders M. Lang, Rixheim, France

[73] Assignee: Ciba-Geigy Corporation, Ardsley, N.Y.

[21] Appl. No.: 3,118

[22] Filed: Jan. 14, 1987

Related U.S. Application Data

[63] Continuation-in-part of Ser. No. 601,763, Apr. 18, 1984, abandoned, which is a continuation-in-part of Ser. No. 549,141, Nov. 7, 1983, abandoned.

[30] Foreign Application Priority Data

Nov. 16, 1982 [CH] Switzerland .................. 6670/82
May 6, 1983 [CH] Switzerland .................. 2490/83

[51] Int. Cl.$^4$ .................. C07D 499/00; A61K 31/415
[52] U.S. Cl. .................................... 514/192; 514/195; 540/310
[58] Field of Search .................. 540/225, 224, 310

[56] References Cited

U.S. PATENT DOCUMENTS

| | | | |
|---|---|---|---|
| 4,272,437 | 6/1981 | Menard | 260/239 A |
| 4,301,074 | 11/1981 | Christensen et al. | 260/242.2 R |
| 4,347,183 | 8/1982 | Afonso et al. | 260/245.2 R |
| 4,395,418 | 7/1983 | Ohki et al. | 424/270 |
| 4,482,565 | 11/1984 | Foglio et al. | 424/270 |
| 4,540,580 | 9/1985 | Afonso et al. | 514/195 |
| 4,617,300 | 10/1986 | Girijavallabhan | 540/310 |
| 4,623,643 | 11/1986 | Alpegiani et al. | 540/310 |

FOREIGN PATENT DOCUMENTS

| | | |
|---|---|---|
| 58317 | 8/1982 | European Pat. Off. . |
| 69373 | 1/1983 | European Pat. Off. . |
| 72014 | 2/1983 | European Pat. Off. . |
| 109044 | 5/1984 | European Pat. Off. . |
| 110826 | 6/1984 | European Pat. Off. . |
| 846832 | 4/1985 | South Africa . |

OTHER PUBLICATIONS

Derwent Abstract of Japanese, 56/166194 (1981).
Derwent Abstract of Japanese, 58/105992 (1983).
The Journal of Antibiotics, vol. 40, No. 2, pp. 217-220 (2/87).
J. Org. Chem., vol. 43, No. 2, pp. 337-339 (1978).
Girijavallabhan et al., Tetrahedron Letters, vol. 22, No. 36, pp. 3485-3488 (1981).

*Primary Examiner*—Nicholas S. Rizzo
*Attorney, Agent, or Firm*—Irving M. Fishman

[57] ABSTRACT

2-Heterocyclyl-lower alkyl-6-hydroxy-lower alkyl-2-penem compounds of the formula

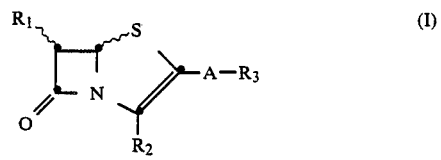

in which $R_1$ represents lower alkyl substituted by hydroxy or protected hydroxy, $R_2$ represents carboxy or functionally modified carboxy, $R_3$ represents an unsaturated monocyclic azaheterocyclyl radical bonded via a tertiary ring nitrogen atom to the radical -A- and A represents a lower alkylene radical, optical isomers of compounds of the formula (I), mixtures of these optical isomers and salts of such compounds of the formula (I) that contain a salt-forming group have antibiotic properties. The novel compounds can be used, for example, in the form of antibiotically active preparations for the treatment of infectious diseases. The novel compounds can be manufactured in a manner known per se.

31 Claims, No Drawings

6-HYDROXY-LOWER ALKYLPENEM COMPOUNDS, PHARMACEUTICAL PREPARATIONS THAT CONTAIN THESE COMPOUNDS, AND THE USE OF THE LATTER

CROSS REFERENCE TO RELATED APPLICATION

This is a continuation-in-part of application Ser. No. 601,763 filed on Apr. 18, 1984, which in turn is a continuation-in-part of application Ser. No. 549,141 filed on Nov. 7, 1983, both now abandoned.

The present invention relates to novel 6-hydroxy-lower alkylpenem compounds, to processes for their manufacture, to pharmaceutical preparations that contain such compounds, and to their use for the manufacture of pharmaceutical preparations or as pharmacologically active compounds.

The invention relates especially to 2-heterocyclyl-lower alkyl-6-hydroxy-lower alkyl-2-penem compounds of the formula

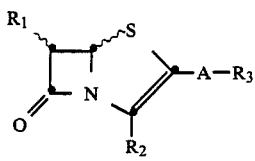

in which
$R_1$ represents lower alkyl substituted by hydroxy or protected hydroxy,
$R_2$ represents carboxy or functionally modified carboxy,
$R_3$ represents an unsaturated monocyclic azaheterocyclyl radical bonded via a tertiary ring nitrogen atom to the radical -A-, and A represents a lower alkylene radical,
to optical isomers of compounds of the formula (I), to mixtures of these optical isomers and to salts of such compounds of the formula (I) having a salt-forming group.

Within the scope of the present description, the definitions used hereinbefore and hereinafter have preferably the following meanings:

Functionally modified carboxy $R_2$ is especially esterified carboxy that can be cleaved under physiological conditions, or protected carboxy $R_2'$.

An esterified carboxy group $R_2$ that can be cleaved under physiological conditions (that is to say metabolisable) protects the compounds of the formula I from salt formation in the gastro-intestinal tract in the case of oral administration, preventing premature excretion. Such groups are known from cephalosporin, penicillin and penem chemistry and are especially acyloxymethoxycarbonyl groups in which acyl represents, for example, the radical of an organic carboxylic acid, especially an optionally substituted lower alkanecarboxylic acid, or in which acyloxymethyl forms the radical of a lactone. Such groups are, for example, lower alkanoyloxymethoxycarbonyl, amino-lower alkanoyloxymethoxycarbonyl, especially α-amino-lower alkanoyloxymethoxycarbonyl, 4-crotonolactonyl and 4-butyrolacton-4-yl. Further esterified carboxy groups $R_2$ that can be cleaved under physiological conditions are, for example, 5-indanyloxycarbonyl, 3-phthalidyloxycarbonyl, 1-lower alkoxycarbonyloxy-lower alkoxycarbonyl, 1-lower alkoxy-lower alkoxycarbonyl or 2-oxo-1,3-dioxolen-4-ylmethoxycarbonyl which is substituted in the 5-position of the dioxolene ring by lower alkyl or phenyl.

An unsaturated monocyclic azaheterocyclyl radical $R_3$ that is bonded via a tertiary ring nitrogen atom to the radical -A- is especially a corresponding optionally partially saturated 5-membered heteroaryl radical having from 1 to 4 ring nitrogen atoms, such as a corresponding aza-, diaza-, triaza- or tetraza-cyclic radical of aromatic character or a corresponding dihydro radical, or a corresponding partially saturated 6-membered heteroaryl radical having from 1 to 3 ring nitrogen atoms, such as a corresponding aza-, diaza- or triaza-cyclic radical, for example a corresponding dihydro or tetrahydro radical. Corresponding radicals $R_3$ are, for example, optionally partially saturated pyrrolyl, diazolyl, triazolyl or tetrazolyl or partially saturated pyridyl, pyrimidyl, pyridazinyl, pyrazinyl or triazinyl. These radicals are unsubstituted or may be substituted, such as, especially, mono- or also poly-substituted, such as, more especially, mono- or di-substituted, by optionally etherified or esterified, including protected, hydroxy, for example hydroxy, lower alkoxy, lower alkanoyloxy or halogen; optionally etherified mercapto, for example mercapto, lower alkylthio or phenylthio; lower alkyl, hydroxy-lower alkyl, lower alkanoyloxy-lower alkyl, carbamoyl-lower alkyl, carbamoyloxy-lower alkyl, halo-lower alkyl, lower alkoxy-lower alkyl, carboxy-lower alkyl, optionally N-lower alkylated amino-lower alkyl, for example amino-lower alkyl, lower alkylamino-lower alkyl or di-lower alkylamino-lower alkyl, lower alkanoylamino-lower alkyl, amino-carboxy-lower alkyl, or sulpho-lower alkyl; optionally substituted, including protected, amino, for example amino, lower alkylamino, di-lower alkylamino, a lower alkyleneamino or acylamino, such as lower alkanoylamino; optionally functionally modified, including protected, carboxy or sulpho, for example carboxy, sulpho, esterified carboxy, such as lower alkoxycarbonyl, optionally substituted carbamoyl, such as N-mono- or N,N-di-lower alkylated carbamoyl, cyano or sulphamoyl; phenyl optionally substituted by lower alkyl, nitro, lower alkoxy and/or halogen; or cycloalkyl, nitro, oxo and/or oxido.

In the present description, the term "lower" used in connection with definitions of groups or compounds denotes that, unless expressly defined otherwise, the groups and compounds so designated contain up to 7, preferably up to 4, carbon atoms.

Lower alkyl substituted by hydroxy as group R is especially lower alkyl substituted by hydroxy in the α-position relative to the penem ring structure and represents, for example, 1-hydroxyprop-1-yl, 2-hydroxyprop-2-yl, 1-hydroxybut-1-yl, 2-hydroxybut-2-yl or, especially, hydroxymethyl or 1-hydroxyethyl Lower alkanoyloxymethoxycarbonyl is, for example, acetoxymethoxycarbonyl or pivaloyloxymethoxycarbonyl.

α-Amino-lower alkanoyloxymethoxycarbonyl is, for example, glycyloxymethoxycarbonyl, valyloxymethoxycarbonyl or leucyloxymethoxycarbonyl.

1-lower alkoxycarbonyloxy-lower alkoxycarbonyl is, for example, ethoxycarbonyloxymethoxycarbonyl or 1-ethoxycarbonyloxyethoxycarbonyl.

1-lower alkoxy-lower alkoxycarbonyl is, for example, methoxymethoxycarbonyl or 1-methoxyethoxycarbonyl.

Lower alkoxy is, for example, methoxy, also ethoxy, n-propoxy, isopropoxy, n-butoxy, isobutoxy or tert.-butoxy, and n-pentyloxy, n-hexyloxy or n-heptyloxy.

Lower alkanoyloxy is, for example, acetoxy or propionyloxy.

Halogen is, for example, fluorine, chlorine, bromine or iodine.

Lower alkylthio is, for example, methylthio, ethylthio, n-propylthio, isopropylthio or n-butylthio.

Lower alkyl as substituent of a radical $R_3$ is, for example, methyl, ethyl, n-propyl, isopropyl, n-butyl, isobutyl, sec.-butyl or tert.-butyl, also n-pentyl, n-hexyl or n-heptyl.

Hydroxy-lower alkyl as substituent of a radical $R_3$ is, for example, hydroxymethyl, 2-hydroxyethyl or 2,3-dihydroxypropyl.

Lower alkanoyloxy-lower alkyl is, for example, acetoxymethyl or 2-acetoxyethyl.

Carbamoyl-lower alkyl is, for example, carbamoylmethyl or 2-carbamoylethyl, whilst carbamoyloxy-lower alkyl is, for example, carbamoyloxymethyl or 2-carbamoyloxyethyl.

Halo-lower alkyl is, for example, chloromethyl, bromomethyl, 2-chloroethyl or 2,2-dichloroethyl.

Lower alkanoylamino-lower alkyl is, for example, acetaminomethyl, 2-acetaminoethyl or formylaminomethyl.

Amino-carboxy-lower alkyl is, for example, 2-amino-2-carboxyethyl or 1-amino-1-carboxymethyl.

Lower alkoxy-lower alkyl is, for example, methoxymethyl, 2-methoxyethyl, ethoxymethyl or 2-ethoxyethyl.

Carboxy-lower alkyl is, for example, carboxymethyl, 1-carboxy-, 2-carboxy- or 1,2-dicarboxy-ethyl.

Amino-lower alkyl is, for example, aminomethyl or 2-aminoethyl, while di-lower alkylamino-lower alkyl is, for example, dimethylaminomethyl, 2-dimethylaminoethyl or 2-diethylaminoethyl.

Sulpho-lower alkyl is, for example, sulphomethyl or 2-sulphoethyl.

Lower alkylamino is, for example, methylamino, ethylamino, n-propylamino, isopropylamino or n-butylamino, while di-lower alkylamino is, for example, dimethylamino, diethylamino, di-n-propylamino or diisopropylamino.

Lower alkyleneamino has especially from 4 to 6 carbon chain members and represents, for example, pyrrolidino or piperidino.

Lower alkanoylamino is, for example, acetylamino or propionylamino.

Lower alkoxycarbonyl is, for example, methoxycarbonyl or ethoxycarbonyl.

N-mono-lower alkylated carbamoyl is, for example, N-methyl-, N-ethyl- or N-propyl-carbamoyl, while N,N-di-lower alkylated carbamoyl represents, for example, N,N-dimethyl- or N,N-diethyl-carbamoyl.

Cycloalkyl contains from 3 to 8, especially 5 or 6, ring members and is, for example, cyclopentyl or cyclohexyl, also cyclopropyl or cycloheptyl.

Preferred esterified carboxy groups $R_2$ that can be cleaved under physiological conditions are, for example, phthalidyloxycarbonyl, lower alkanoyloxymethoxycarbonyl, for example pivaloyloxymethoxycarbonyl, and 1-lower alkoxycarbonyloxy-lower alkoxycarbonyl, for example 1-ethoxycarbonyloxyethoxycarbonyl.

Corresponding 5-membered optionally partially saturated heteroaryl radicals $R_3$ are, for example, pyrrolyl or dihydropyrrolyl optionally substituted, for example, by lower alkyl or halogen, for example 1-pyrrolyl, 3-methyl-1-pyrrolyl, 3,4-dichloro-1pyrrolyl, also 2,3- or 2,5-dihydro-1-pyrrolyl; diazolyl, such as imidazolyl or pyrazolyl, for example 1-imidazolyl or 1-pyrazolyl, optionally substituted, for example, by lower alkyl, amino-lower alkyl, amino or nitro; triazolyl, such as 1H-1,2,3-triazol-1-yl, 2H-1,2,3-triazol-2-yl, 1H-1,2,4-triazol-1-yl or 1H1,3,4-triazol-1-yl, optionally substituted, for example, by lower alkyl, carboxy-lower alkyl, amino or phenyl, for example the corresponding unsubstituted radicals, 4- or 5-methyl-1,2,3-triazol-1-yl, 3-methyl- or 3-phenyl-1H-1,2,4-triazol-1-yl; or tetrazolyl, such as 1H-tetrazol-1-yl or 2H-tetrazol-2-yl, optionally substituted, for example, by lower alkyl, carboxy-lower alkyl, sulpho-lower alkyl, di-lower alkylamino-lower alkyl, amino or by phenyl optionally substituted by halogen, for example the corresponding unsubstituted radicals, 5-amino-, 5-methyl-, 5-carboxymethyl-, 5-(2-carboxyethyl)-, 5-sulphomethyl-, 5-(2-dimethylaminoethyl)- or 5-phenyl-1H-tetrazol-1-yl, or 5-amino-, 5-methyl-, 5-carboxymethyl-, 5-sulphomethyl-, 5-(2-dimethylaminoethyl)- or 5-phenyl-2H-tetrazol-2-yl.

Corresponding 6-membered partially saturated heteroaryl radicals $R_3$ are, for example, dihydro-1-pyridyl, such as 2H-1,2-dihydro- or 4H-1,4-dihydro--pyridyl, that is unsubstituted or, especially, substituted by, for example, oxo and optionally additionally substituted by halogen, for example 2-oxo-2H-1,2-dihydro-1-pyridyl or 4-oxo-4H-1,4-dihydro-1-pyridyl; dihydro-1-pyrimidyl, such as 2H-1,2-dihydro- or 4H-1,4-dihydro-1-pyrimidyl, optionally substituted, for example, especially by oxo, and optionally additionally substituted, for example, by lower alkyl, amino, di-lower alkylamino or carboxy, for example 2-oxo-1,2-dihydro-1-pyrimidyl, 6-methyl-, 5-methyl-, 6-amino-, 6-dimethylamino-, 5-carboxy- or 6-carboxy-2-oxo-1,2-dihydro-1-pyrimidyl or 4-oxo-1,4-dihydro-1-pyrimidyl; or dihydro- or tetrahydro-triazinyl, for example 2H-1,2-dihydro-1,3,5-triazin-1-yl, 2H-1,2-dihydro-1,2,4-triazin-1-yl, 2H-1,2,5,6-tetrahydro-1,2,4-triazin-1-yl or 4H-1,4,5,6-tetrahydro-1,2,4,-triazin-1-yl, optionally substituted, for example, by lower alkyl and/or by up to 2 oxo groups, for example 4-lower alkyl-1,4,5,6-tetrahydro-5,6-dioxo-1,2,4-triazin-1-yl, for example 4-methyl-1,4,5,6-tetrahydro- 5,6-dioxo-1,2,4-triazin-1-yl.

A lower alkylene radical A is straight-chained lower alkylene of the formula $-(CH_2)_m-$ wherein m is an integer from 1 to 12, more especially from 1 to 7, and preferably from 1 to 4, or such straight-chained lower alkylene of the formula $-(CH_2)_m-$ wherein m is an integer from 1 to 7 that is substituted, such as mono- or polysubstituted, especially mono- or di-substituted, by lower alkyl having from 1 to 4 carbon atoms, especially having 1 or 2 carbon atoms. Such a straight-chained lower alkylene group is, for example, methylene, ethylene, 1,3-propylene, 1,4-butylene, and also 1,5-pentylene, 1,7-heptylen or 1,10-decylen, and such lower alkyl is, for example, n-propyl, n-butyl or, especially, methyl or ethyl. Two lower alkyl substituents may be located at the same carbon atom (geminal), at adjacent carbon atoms (vicinal) or at different carbon atoms, separated by at least one methylene group, of the lower alkylene chain.

Such a radical A is, for example, straight-chained lower alkylene, such as methylene, ethylene, 1,3-propylene, 1,4-butylene, 1,5-pentylen, 1,7-heptylen or 1,10-decylen; lower alkylidene, such as ethylidene ("methylmethylene"), 1,2-propylene, 2-lower alkyl-1,2-propylene, such as 2-methyl-1,2-propylene, 1,2-butylene, 2-lower alkyl-1,2-butylene, such as 2-methyl- or 2-ethyl-1,2-butylene, 3-lower alkyl-1,2-butylene, such as 3-methyl-1,2-butylene, 1,3-butylene, 2-lower alkyl-1,3-butylene, such as 2-methyl-1,3-butylene, 3-lower alkyl-1,3-butylene, such as 3-methyl-1,3-butylene, or 2,2-di-lower alkyl-1,3-butylene, such as 2,2-dimethyl-1,3-butylene, carbon atom 1 in these radicals being bonded to the penem ring structure; or also 1,2-propylene, 2-lower alkyl-1,2-propylene, such as 2-methyl-1,2-propylene, 1,2-butylene, 2-lower alkyl-1,2-butylene, such as 2-methyl- or 2-ethyl-1,2-butylene, 3-lower alkyl-1,2-butylene, such as 3-methyl-1,2-butylene, or 3,3-di-lower alkyl-1,2-butylene, such as 3,3-dimethyl-1,2butylene, carbon atom 2 in these radicals being bonded to the penem ring structure.

Preferred radicals A are methylene, ethylene, 1,3-propylene, 1,4-butylene, 1,7-heptylen or ethylidene, 1,2-propylene, 1,2-butylene, 1,3-butylene and 2-methyl-1,2-propylene bonded via carbon atom 1 to the penem ring structure, and 1,2-propylene bonded via carbon atom 2 to the penem ring structure.

In a further preferred embodiment the invention relates to 2-heterocyclylalkyl-2-penem compounds of the formula

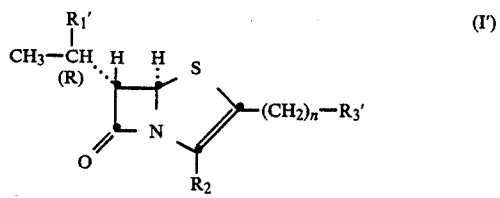

in which $R_1'$ represents hydroxy or protected hydroxy, $R_2$ represents carboxy or functionally modified carboxy, $R_3'$ represents a monocyclic heteroaryl radical bonded via a ring nitrogen atom and having from 1 to 4 ring nitrogen atoms and n represents an integer from 3 to 12, to salts of compounds of the formula I, to processes for the manufacture of compounds of the formula I, to pharmaceutical preparations that contain such compounds and to their use for the manufacture of pharmaceutical preparations or as pharmacologically active compounds.

Functionally modified carboxy $R_2$ has the meanings specified above.

A monocyclic heteroaryl radical $R_3'$ bonded via a ring nitrogen atom and having from 1 to 4 ring nitrogen atoms is especially a corresponding 5-membered heteroaryl radical, that is to say a corresponding aza-, diaza-, triaza- or tetraza-cyclic radical of aromatic character. Corresponding heteroaryl radicals $R_3'$ are, for example, 1-pyrrolyl, 1-diazolyl, such as 1-imidazolyl or 1-pyrazolyl, 1,2,4- or 1,3,4-triazol-1-yl or 1- or 2-tetrazolyl. Such radicals are unsubstituted or substituted as specified above (see definition of radical $R_3$).

Preferred radicals $R_3'$ are, for example, 1-pyrrolyl that is unsubstituted or substituted by lower alkyl, such as methyl, 1-pyrazolyl that is unsubstituted or substituted by lower alkyl, such as methyl, or by halogen, such as chlorine, 1-imidazolyl that is unsubstituted or substituted by lower alkyl, such as methyl, lower alkanoyloxy-lower alkyl, such as acetoxymethyl, halo-lower alkyl, such as chloromethyl, amino-lower alkyl, such as aminomethyl or 2-aminoethyl, lower alkanoylamino-lower alkyl, such as 2-acetylaminoethyl, and/or by lower alkoxy, such as methoxy, 1,2,4- or 1,3,4-triazol-1-yl that is unsubstituted or substituted by lower alkyl, such as methyl, or by lower alkoxycarbonyl, such as methoxycarbonyl, and 1- or 2-tetrazolyl that is unsubstituted or substituted by lower alkyl, such as methyl.

In preferred compounds of the formula I', n is an integer from 3 to 8.

The functional groups present in compounds of the formula I and I', such as hydroxy, carboxy, amino or sulpho groups, especially the hydroxy group $R_1'$ or the hydroxy group in the radical $R_1$ and the carboxy group $R_2$, are optionally protected by conventional protecting groups used in penem, penicillin, cephalosporin and peptide chemistry.

Such protecting groups can be removed readily, that is to say, without undesirable secondary reactions taking place, for example by means of solvolysis or reduction, or alternatively under physiological conditions.

Protecting groups of this type and the methods by which they are introduced and removed are described, for example, in J. F. W. McOmie, "Protective Groups in Organic Chemistry", Plenum Press, London, New York, 1973, T. W. Greene, "Protective Groups in Organic Synthesis", Wiley, New York, 1981, "The Peptides", Vol. I, Schroeder und Luebke, Academic Press, London, New York, 1965 and Houben-Weyl, "Methoden der Organischen Chemie", Volume 15/1, Georg Thieme Verlag, Stuttgart, 1974.

In compounds of the formula (I) or (I') the hydroxy group $R_1'$, a hydroxy group in the radical $R_1$, and a hydroxy group present in in the radical $R_3$ or $R_3'$, may be protected, for example, by acyl radicals. Suitable acyl radicals are, for example, lower alkanoyl optionally substituted by halogen, for example acetyl or trifluoroacetyl, benzoyl optionally substituted by nitro, for example benzoyl, 4-nitrobenzoyl or 2,4-dinitrobenzoyl, lower alkoxycarbonyl optionally substituted by halogen, for example 2-bromoethoxycarbonyl or 2,2,2-trichloroethoxycarbonyl, lower alkenyloxycarbonyl, for example allyloxycarbonyl, lower alkenyloxyoxalyl, for example allyloxyoxalyl, or phenyl-lower alkoxycarbonyl optionally substituted by nitro, for example 4-nitrobenzyloxycarbonyl. Further suitable hydroxy-protecting groups are, for example, tri-substituted silyl, such as tri-lower alkylsilyl, for example trimethylsilyl, dimethyl-(2,3-dimethylbutyl)-silyl, or tert.-butyldimethylsilyl, 2-halo-lower alkyl groups, for example 2-chloro-, 2-bromo-, 2-iodo- and 2,2,2-trichloro-ethyl, and phenyl-lower alkyl optionally substituted by halogen, for example chlorine, lower alkoxy, for example methoxy, and/or by nitro, such as corresponding benzyl. Tri-lower alkylsilyl, lower alkenyloxycarbonyl and lower alkenyloxyoxalyl are preferred as hydroxy-protecting group.

A carboxy group $R_2$ and also a carboxy group present in the radical $R_3$ or $R_3'$ is customarily protected in esterified form, the ester group being readily cleavable under mild conditions, for example under mildly reductive, such as hydrogenolytic, conditions, or under mildly solvolytic, such as acidolytic or especially basic or neutral hydrolytic, conditions. A protected carboxy group can also be an esterified carboxy group that can be readily converted into a different functionally modified carboxy group, such as into a different esterified carboxy group.

Such esterified carboxy groups contain as esterifying groups especially lower alkyl groups that are branched in the 1-position or suitably substituted in the 1- or 2-position. Preferred carboxy groups in esterified form are, inter alia, lower alkoxycarbonyl, for example methoxycarbonyl, ethoxycarbonyl, isopropoxycarbonyl or tert.-butoxycarbonyl, and (hetero)arylmethoxycarbonyl having from 1 to 3 aryl radicals or having a monocyclic heteroaryl radical, these optionally being mono- or poly-substituted, for example by lower alkyl, such as tert.-lower alkyl, for example tert.-butyl, halogen, for example chlorine, and/or by nitro. Examples of such groups are benzyloxycarbonyl optionally substituted, for example, as mentioned above, for example 4-nitrobenzyloxycarbonyl, diphenylmethoxycarbonyl or triphenylmethoxycarbonyl optionally substituted, for example, as mentioned above, for example diphenylmethoxycarbonyl, or picolyloxycarbonyl, for example 4-picolyloxycarbonyl, or furfuryloxycarbonyl, such as 2-furfuryloxycarbonyl, both optionally substituted, for example, as mentioned above. Further suitable groups are lower alkanoylmethoxycarbonyl, such as acetonyloxycarbonyl, aroylmethoxycarbonyl, in which the aroyl group preferably represents benzoyl optionally substituted, for example, by halogen, such as bromine, for example phenacyloxycarbonyl, halo-lower alkoxycarbonyl, such as 2-halo-lower alkoxycarbonyl, for example 2,2,2-trichloroethoxycarbonyl, 2-chloroethoxycarbonyl, 2-bromoethoxycarbonyl or 2-iodoethoxycarbonyl, or ω-halo-lower alkoxycarbonyl in which lower alkoxy contains from 4 to 7 carbon atoms, for example 4-chlorobutoxycarbonyl, lower alkenyloxycarbonyl, for example allyloxycarbonyl, phthalimidomethoxycarbonyl, lower alkenyloxycarbonyl, for example allyloxycarbonyl, or ethoxycarbonyl substituted in the 2-position by lower alkylsulphonyl, cyano or by tri-substituted silyl, such as tri-lower alkylsilyl or triphenylsilyl, for example 2-methylsulphonylethoxycarbonyl, 2-cyanoethoxycarbonyl, 2-trimethylsilylethoxycarbonyl or 2-(di-n-butyl-methyl- silyl)-ethoxycarbonyl.

Other protected carboxy groups in esterified form are corresponding organic silyloxycarbonyl groups, and also corresponding organic stannyloxycarbonyl groups. In these groups the silicon or tin atom preferably has lower alkyl, especially methyl or ethyl, and also lower alkoxy, for example methoxy, as substituents. Suitable silyl and stannyl protecting groups are especially tri-lower alkylsilyl, especially trimethylsilyl or dimethyl-tert.-butylsilyl, or correspondingly substituted stannyl groups, for example tri-n-butylstannyl.

Preferred protected carboxy groups are the 4-nitrobenzyloxycarbonyl or the lower alkenyloxycarbonyl group or the ethoxycarbonyl group substituted in the 2-position by tri-lower alkylsilyl.

A protected amino group can be, for example, in the form of a readily cleavable acylamino, acylimino, etherified mercaptoamino, silylamino or stannylamino group or in the form of an enamino, nitro or azido group.

In a corresponding acylamino group, acyl is, for example, the acyl radical of an organic acid having, for example, up to 18, more especially up to 12, carbon atoms, especially an alkanecarboxylic acid optionally substituted, for example, by halogen or phenyl, or of a benzoic acid optionally substituted, for example, by halogen, lower alkoxy or nitro, or of a carbonic acid semiester. Such acyl groups are, for example, lower alkanoyl, such as formyl, acetyl or propionyl, halo-lower alkanoyl, such as 2-haloacetyl, especially 2-fluoro-, 2-bromo-, 2-iodo-, 2,2,2-trifluoro- or 2,2,2-trichloro-acetyl, optionally substituted benzoyl, for example benzoyl, halobenzoyl, such as 4-chlorobenzoyl, lower alkoxybenzoyl, such as 4-methoxybenzoyl, or nitrobenzoyl, such as 4-nitrobenzoyl. Especially suitable are also lower alkenyloxycarbonyl, for example allyloxycarbonyl, or lower alkoxycarbonyl optionally substituted in the 1- or 2-position, such as lower alkoxycarbonyl, for example methoxy- or ethoxy-carbonyl, optionally substituted benzyloxycarbonyl, for example benzyloxycarbonyl or 4-nitrobenzyloxycarbonyl, aroylmethoxycarbonyl in which the aroyl group preferably represents benzoyl optionally substituted, for example, by halogen, such as bromine, for example phenacyloxycarbonyl, 2-halo-lower alkoxycarbonyl, for example 2,2,2-trichloroethoxycarbonyl, 2-chloroethoxycarbonyl, 2-bromoethoxycarbonyl or 2-iodoethoxycarbonyl, or 2-(trisubstituted silyl)-ethoxycarbonyl, such as 2-tri-lower alkylsilylethoxycarbonyl, for example 2-trimethylsilylethoxycarbonyl or 2-(di-n-butyl-methylsilyl)-ethoxycarbonyl, or 2-triarylsilylethoxycarbonyl, such as 2-triphenylsilylethoxycarbonyl.

In an acylimino group, acyl is, for example, the acyl radical of an organic dicarboxylic acid having, for example, up to 12 carbon atoms, especially of a corresponding aromatic dicarboxylic acid, such as phthalic acid. Such a group is especially phthalimino.

An etherified mercaptoamino group is especially a phenylthioamino group optionally substituted by lower alkyl, such as methyl or tert.-butyl, lower alkoxy, such as methoxy, halogen, such as chlorine or bromine, and/or by nitro, or a pyridylthioamino group. Corresponding groups are, for example, 2- or 4-nitrophenylthioamino or 2-pyridylthioamino.

A silyl- or stannyl-amino group is especially an organic silyl- or stannyl-amino group in which the silicon or tin atom preferably has substituent(s) selected from lower alkyl, for example methyl, ethyl, n-butyl or tert.-butyl, also lower alkoxy, for example methoxy. Corresponding silyl or stannyl groups are especially tri-lower alkylsilyl, especially trimethylsilyl, also dimethyl-tert.-butylsilyl, or correspondingly substituted stannyl, for example tri-n-butylstannyl.

Further protected amino groups are, for example, enamino groups that contain an electron-attracting substituent, for example a carbonyl group, at the double bond in the 2-position Protecting groups of this type are, for example, 1-acyl-lower alk-1-en-2-yl radicals in which acyl represents, for example, the corresponding radical of a lower alkanecarboxylic acid, for example acetic acid, of a benzoic acid optionally substituted, for example, by lower alkyl, such as methyl or tert.-butyl, lower alkoxy, such as methoxy, halogen, such as chlorine, and/or by nitro, or especially of a carbonic acid semiester, such as a carbonic acid-lower alkyl semiester, for example a carbonic acid methyl semiester or ethyl semiester, and in which lower alk-1-ene represents especially 1-propene. Corresponding protecting groups are especially 1-lower alkanoylprop-1-en-2-yl, for example 1-acetylprop-1-en-2-yl, or 1-lower alkoxycarbonylprop-1-en-2-yl, for example 1-ethoxycarbonylprop-1-en-2-yl.

A protected sulpho group in the radical $R_3$ or $R_3'$ is especially an esterified sulpho group, such as a sulpho group esterified by an aliphatic, cycloaliphatic, cycloaliphatic-aliphatic, aromatic or araliphatic alcohol, for example a lower alkanol, or by a silyl or stannyl radical, such as tri-lower alkylsilyl. In a sulpho group the hydroxy group may be etherified, for example in the same manner as the hydroxy group in an esterified carboxy group.

Salts of compounds according to the invention are especially pharmaceutically acceptable, non-toxic salts of compounds of the formula I. Such salts are formed, for example, from the acidic groups present in compounds of the formula I, for example carboxy and sulpho groups, and are especially metal or ammonium salts, such as alkali metal and alkaline earth metal salts, for example sodium, potassium, magnesium or calcium salts, and ammonium salts with ammonia or suitable organic amines, such as lower alkylamines, for example triethylamine, hydroxy-lower alkylamines, for example 2-hydroxyethylamine, bis-(2-hydroxyethyl)-amine or tris-(2-hydroxyethyl)-amine, basic aliphatic esters of carboxylic acids, for example 4-aminobenzoic acid 2-diethylaminoethyl ester, lower alkyleneamines, for example 1-ethylpiperidine, cycloalkylamines, for example dicyclohexylamine, or benzylamines, for example N,N'-dibenzylethylenediamine, dibenzylamine or N-benzyl-β-phenethylamine. Compounds of the formula I having a basic group, for example having an amino group, can form acid addition salts, for example with inorganic acids, such as hydrochloric acid, sulphuric acid or phosphoric acid, or with suitable organic carboxylic or sulphonic acids, for example acetic acid, succinic acid, fumaric acid, maleic acid, tartaric acid, oxalic acid, citric acid, benzoic acid, mandelic acid, malic acid, ascorbic acid, methanesulphonic acid or 4-toluenesulphonic acid. Compounds of the formula I having an acidic group and a basic group can also be in the form of internal salts, that is to say in zwitterionic form.

For the purposes of isolation or purification it is also possible to use pharmaceutically unacceptable salts. Only the pharmaceutically acceptable, non-toxic salts are used therapeutically and these are therefore preferred.

In the penem compounds of the formula I, the two asymmetric carbon atoms in the 5- and 6-positions can be in the R-, the S- or the racemic R,S-configuration. The compounds in which the configuration of the 5-carbon atom corresponds to that of natural penicillin (5R-configuration) are preferred. The hydrogen atoms in the 5- and 6-positions can be in the cis- or, preferably, in the trans-position with respect to one another. In the preferred configuration the substituent in the 6-position assumes the S-configuration. The compounds of the formula I can have further chirality centres in the radicals $R_1$ and/or A each of which can be in the R-configuration, the S-configuration or the R,S-configuration. Lower alkyl $R_1$ substituted in the α-position by hydroxy preferably has the R-configuration.

The invention relates especially to compounds of the formula I in which $R_1$ represents lower alkyl substituted by hydroxy or protected hydroxy, $R_2$ represents carboxy, esterified carboxy that can be cleaved under physiological conditions, or protected carboxy $R_2'$, $R_3$ represents a monocyclic, optionally partially saturated, 5-membered heteroaryl radical having from 1 to 4 ring nitrogen atoms that is bonded via a tertiary ring nitrogen atom to the radical -A-, such as a corresponding aza-, diaza-, triaza- or tetraza-cyclic radical of aromatic character or a corresponding dihydro radical, or a corresponding partially saturated 6-membered heteroaryl radical having from 1 to 3 ring nitrogen atoms, such as a corresponding aza-, diaza- or triaza-cyclic radical, for example a corresponding dihydro or tetrahydro radical, these radicals being unsubstituted or substituted by hydroxy, lower alkoxy, lower alkanoyloxy, halogen, mercapto, lower alkylthio, phenylthio, lower alkyl, hydroxy-lower alkyl, lower alkoxy-lower alkyl, carboxy-lower alkyl, amino-lower alkyl, di-lower alkylamino-lower alkyl, sulpho-lower alkyl, amino, lower alkylamino, di-lower alkylamino, lower alkyleneamino, lower alkanoylamino, carboxy, lower alkoxycarbonyl, optionally N-mono- or N,N-di-lower alkylated carbamoyl, cyano, sulpho, sulphamoyl, phenyl optionally substituted by lower alkyl, nitro, lower alkoxy and/or by halogen, cycloalkyl, nitro, oxo and/or oxido, and A represents straight-chained lower alkylene substituted by lower alkyl, to optical isomers of compounds of the formula (I), to mixtures of these optical isomers, and to salts of compounds of the formula (I) that have a salt-forming group. The invention relates also especially to compounds of the formula (I) in which $R_1$ represents methyl or ethyl substituted by hydroxy or protected hydroxy, $R_2$ and $R_3$ have the above meanings and A represents straight-chained lower alkylene having from 1 to 4 carbon atoms, to optical isomers of compounds of the formula (I), to mixtures of these optical isomers, and to salts of compounds of the formula (I) that have a salt-forming group.

The invention relates more especially to compounds of the formula (I) in which $R_1$ represents lower alkyl substituted by hydroxy or tri-lower alkylsilyloxy, $R_2$ represents carboxy, lower alkenyloxycarbonyl, benzyloxycarbonyl optionally substituted by nitro, 2-tri-lower alkylsilylethoxycarbonyl or an esterified carboxy group that can be cleaved under physiological conditions, for example 1-lower alkoxycarbonyloxy-lower alkoxycarbonyl, lower alkanoyloxymethoxycarbonyl, α-amino-lower alkanoyloxymethoxycarbonyl or phthalidyloxycarbonyl, $R_3$ represents one of the following groups, each of which is bonded via a tertiary ring nitrogen atom to the radical -A-: pyrrolyl, for example 1-pyrrolyl, that is unsubstiuted or substituted by lower alkyl or halogen, imidazolyl or pyrazolyl, for example 1-imidazolyl or 1-pyrazolyl, that is unsubstituted or substituted by lower alkyl, triazolyl, for example 1H-1,2,3-triazol-1-yl, 2H-1,2,3-triazol-2-yl, 1H-1,2,4-triazol-1-yl or 1H-1,3,4-triazol-1-yl, that is unsubstituted or substituted by lower alkyl, carboxy-lower alkyl or phenyl, tetrazolyl, such as 1H-tetrazol-1-yl or 2H-tetrazol-2-yl, that is unsubstituted or substituted by lower alkyl, carboxy-lower alkyl, sulpho-lower alkyl, di-lower alkylamino-lower alkyl, amino, or by phenyl optionally substituted by halogen, dihydro-1-pyridyl, for example 2H-1,2-dihydro-1-pyridyl or 4H-1,4-dihydro-1-pyridyl, that is unsubstituted or substituted by oxo and optionally additionally substituted by halogen, dihydro-1-pyrimidyl, for example 2H-1,2-dihydro-1-pyrimidyl or 4H-1,4-dihydro-1-pyrimidyl, that is unsubstituted or substituted by oxo and optionally additionally substituted by lower alkyl, amino, di-lower alkylamino or carboxy, or dihydro- or tetrahydrotriazinyl, for example 2H-1,2-dihydro-1,3,5-triazin-1-yl, 2H-1,2-dihydro-1,2,4-triazin-1-yl, 2H-1,2,5,6-tetrahydro-1,2,4-triazin-1-yl or 4H-1,4,5,6-tetrahydro-1,2,4-triazin-1-yl, that is unsubstituted or substituted by lower alkyl and/or by up to two oxo groups, and A represents straight-chained lower alkylene substituted by lower alkyl, to optical isomers of compounds of the formula (I), to mixtures of these optical isomers, and to salts, especially pharmaceutically acceptable salts, of such compounds of the formula (I) that contain a salt-forming group. The invention relates also more especially to compounds of the formula (I) in which $R_1$ represents methyl or ethyl substituted by hydroxy or protected hydroxy, $R_2$ and $R_3$ have the above meanings and A represents straight-chained lower alkylene having from 1 to 4 carbon atoms, to optical isomers of compounds of the formula (I), to mixtures of these optical isomers, and to salts, especially pharmaceutically acceptable salts, of such compounds of the formula (I) that contain a salt-forming group.

The invention relates above all to compounds of the formula (I) in which $R_1$ represents hydroxymethyl or hydroxyethyl, $R_2$ represents carboxy, 1-lower alkoxycarbonyloxy-lower alkoxycarbonyl or lower alkanoyloxymethoxycarbonyl, $R_3$ represents one of the following groups each of which is bonded via a tertiary nitrogen atom to the radical -A-: pyrrolyl, imidazolyl, for example 1-imidazolyl, triazolyl, for example 1H-1,2,4-triazol-1-yl, that is optionally substituted by lower alkyl, carboxy-lower alkyl or phenyl, or tetrazolyl, for example 1H-tetrazol-1-yl or 2H-tetrazol-2-yl, that is unsubstituted or substituted by amino, lower alkyl, carboxy-lower alkyl, sulpho-lower alkyl or di-lower alkylamino-lower alkyl, and A represents straight-chained lower alkylene having from 1 to 4 carbon atoms that is mono- or di-substituted by lower alkyl having 1 or 2 carbon atoms, to optical isomers of compounds of the formula (I), for example the (5R,6S)-isomer, to mixtures of these optical isomers and to pharmaceutically acceptable salts of such compounds of the formula (I) that have a salt-forming group. The invention relates also above all to compounds of the formula (I) in which $R_1$ and $R_2$ have the above meanings, $R_3$ represents one of the following groups each of which is bonded via a tertiary nitrogen atom to the radical -A-: triazolyl, for example 1H-1,2,4-triazol-1-yl, that is optionally substituted by lower alkyl, carboxy-lower alkyl or phenyl, or tetrazolyl, for example 1H-tetrazol-1-yl or 2H-tetrazol-2-yl, that is unsubstituted or substituted by amino, lower alkyl, carboxy-lower alkyl, sulpho-lower alkyl or di-lower alkylamino-lower alkyl, and A represents straight-chained lower alkylene having from 1 to 4 carbon atoms, to optical isomers of compounds of the formula (I), for example the (5R,6S)-isomer, to mixtures of these optical isomers and to pharmaceutically acceptable salts of such compounds of the formula (I) that have a salt-forming group.

The invention relates especially to (5R,6S)-configured compounds of the formula (I) in which $R_1$ represents hydroxymethyl or 1-hydroxyethyl, $R_2$ represents carboxy, $R_3$ represents 1-H-tetrazol-1-yl, 1H-1,2,4-triazol-1-yl or pyrrol-1-yl and A represents 1,2-propylene, and to pharmaceutically acceptable salts thereof. The invention relates also especially to (5R-,6S)-configured compounds of the formula (I) in which $R_1$ represents hydroxymethyl, $R_2$ represents carboxy, $R_3$ represents 1H-tetrazol-1-yl or 1H-1,2,4-triazol-1-yl and A represents straight-chained lower alkylene having from 1 to 4 carbon atoms, and to pharmaceutically acceptable salts thereof.

The invention relates furthermore to the pure optical isomers of those compounds of the formula I that have further chirality centres in the substituents $R_1$ and/or A, and to pharmaceutically acceptable salts thereof.

The invention relates furthermore especially to compounds of the formula I' in which $R_1$ I' *represents hydroxy or protected hydroxy*, $R_2$ represents carboxy, esterified carboxy that can be cleaved under physiological conditions or protected carboxy, $R_3'$ represents a monocyclic 5-membered heteroaryl radical that is bonded via a ring nitrogen atom and has from 1 to 4 ring nitrogen atoms and that is unsubstituted or substituted by hydroxy, lower alkoxy, lower alkanoyloxy, halogen, mercapto, lower alkylthio, phenylthio, lower alkyl, hydroxy-lower alkyl, lower alkanoyloxy-lower alkyl, carboxy-lower alkyl, carbamoyl-lower alkyl, carbamoyloxy-lower alkyl, halo-lower alkyl, amino-lower alkyl, lower alkylamino-lower alkyl, di-lower alkylamino-lower alkyl, lower alkanoylamino-lower alkyl, amino-carboxy-lower alkyl, sulpho-lower alkyl, amino, lower alkylamino, di-lower alkylamino, lower alkanoylamino, carboxy, lower alkoxycarbonyl, carbamoyl, cyano, sulpho, sulphamoyl and/or by phenyl that is optionally substituted by lower alkyl, lower alkoxy and/or halogen, and n represents an integer from 3 to 12, and to salts of compounds of the formula I'.

The invention relates more especially to compounds of the formula I' in which $R_1'$ represents hydroxy, $R_2$ represents carboxy or esterified carboxy that can be cleaved under physiological conditions, $R_3'$ represents 1-pyrrolyl that is unsubstituted or substituted by lower alkyl, 1-pyrazolyl that is unsubstituted or substituted by lower alkyl or by halogen, 1-imidazolyl ( that is unsubstituted or substituted by lower alkyl, lower alkanoyloxy-lower alkyl, halo-lower alkyl, amino-lower alkyl, lower alkanoylamino-lower alkyl and/or by lower alkoxy, 1,2,4- or 1,3,4-triazol-1-yl that is unsubstituted or substituted by lower alkyl or by lower alkoxycarbonyl, or 1- or 2-tetrazolyl that is unsubstituted or substituted by lower alkyl, and n represents an integer from 3 to 10, and to salts of compounds of the formula I'.

The invention relates very especially to compounds of the formula I' in which $R_1'$ represents hydroxy, $R_2$ represents carboxy or esterified carboxy that can be cleaved under physiological conditions, $R_3'$ represents 1-tetrazolyl, and n represents an integer from 3 to 8, and to salts of compounds of the formula I'.

In one preferred group of compounds of the formula I' n is an integer from 3 to 4. In another preferred group of compounds of the formula I' n is an integer from 5 to 12.

The invention relates especially to the compounds of the formula (I) and (I') mentioned in the Examples and to their pharmaceutically acceptable salts.

The compounds of the present invention can be manufactured by methods known per se.

The novel compounds are manufactured, for example, as follows:

(a) an ylide compound of the formula

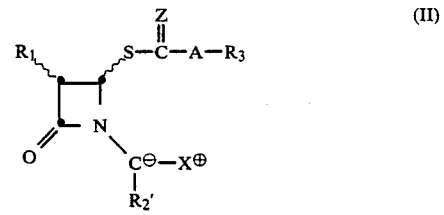

(II)

in which $R_1$, $R_3$ and A have the meanings given under formula (I), $R_2'$ represents a protected carboxy group, Z represents oxygen or sulphur and $X^\oplus$ represents either a trisubstituted phosphonio group, or a diesterified phosphono group together with a cation, is cyclised, or (b) a compound of the formula

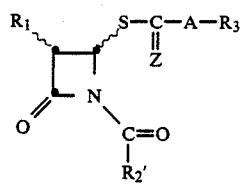

(III)

in which $R_1$, $R_3$ and A have the meanings given under formula (I), Z represents oxygen or sulphur and $R_2'$ represents a protected carboxy group treated with an organic compound of trivalent phosphorus, or (c) a compound of the formula

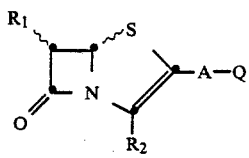

(IV)

in which $R_1$, $R_2$ and A have the meanings given under formula (I) and Q represents a reactive esterified hydroxy group, is reacted with an agent that introduces the azaheterocyclyl radical $R_3$, and, if desired or necessary, in a resulting compound of the formula (I) a protected hydroxy group in the radical $R_1$ is converted into the free hydroxy group and/or, if desired, in a resulting compound of the formula (I) a protected carboxy group $R_2'$ is converted into the free carboxy group, into an esterified carboxy group that can be cleaved under physiological conditions or into a different protected carboxy group $R_2'$ and/or, if desired, a free carboxy group $R_2$ is converted into an esterified carboxy group that can be cleaved under physiological conditions and/or, if desired, other protected functional groups in the radical $R_3$ are converted into the free functional groups and/or, if desired, in a resulting compound of the formula (I) a radical $R_3$ is converted into a different radical $R_3$ and/or, if desired, a resulting compound having a salt-forming group is converted into a salt, or a resulting salt is converted into the free compound or into a different salt and/or, if desired, a resulting mixture of isomeric compounds is separated into the individual isomers.

In starting compounds of the formulae (II) and (III) functional groups additionally present in the radical $R_3$, are preferably protected by conventional protecting groups, for example those mentioned above.

In an analogous manner compounds of the formula I' can be prepared starting with compounds of the formula II or III in which the group —A—R is replaced with —(CH$_2$)$_n$—R$_3'$.

(a) Cyclisation of the Compound of the Formula II

The group $X^\oplus$ in the starting material of the formula II is one of the phosphonio or phosphono groups customarily used in Wittig condensation reactions, especially a triaryl-, for example triphenyl- , or tri-lower alkyl-, for example tri-n-butyl-phosphonio group, or a phosphono group diesterified by lower alkyl, for example ethyl, the symbol $X^\oplus$ in the case of the phosphono group including in addition the cation of a strong base, especially a suitable metal ion, such as an alkali metal ion, for example a lithium, sodium or potassium ion. Preferred as the group $X^\oplus$ is, on the one hand, triphenylphosphonio and, on the other hand, diethylphosphono together with an alkali metal ion, for example a sodium ion.

The ylide compounds of the formula II are, in the isomeric ylene form, also termed phosphorane compounds. In phosphonio compounds of the formula II, the negative charge is neutralised by the positively charged phosphonio group. In phosphono compounds of the formula II, the negative charge is neutralised by the cation of a strong base, which, depending upon the method of manufacture of the phosphono starting material, may be, for example, an alkali metal ion, for example a sodium, lithium or potassium ion. The phosphono starting materials are therefore used as salts in the reaction Cyclisation may take place spontaneously, that is to say in the manufacture of the starting materials, or be effected by heating, for example in a temperature range of approximately from 30° to 160° C., preferably from approximately 50° to approximately 110° C. The reaction is preferably carried out in a suitable inert solvent, such as an aliphatic, cycloaliphatic or aromatic hydrocarbon, for example hexane or benzene, a halogenated hydrocarbon, for example methylene chloride, an ether, for example diethyl ether, a cyclic ether, for example dioxan, a carboxylic acid amide, for example dimethylformamide, a di-lower alkyl sulphoxide, for example dimethyl sulphoxide, or a lower alkanol, for example methanol, or in a mixture thereof, and, if necessary, in an inert gas atmosphere, for example a nitrogen atmosphere.

(b) Cyclisation of the Compound of the Formula III

An organic compound of trivalent phosphorus is derived, for example, from phosphorous acid and is especially an ester thereof with a lower alkanol, for example methanol or ethanol, and/or an optionally substituted aromatic hydroxy compound, for example phenol or pyrocatechol, or an amide ester thereof of the formula $P(OR_a)_2$—$N(R_b)_2$ in which each of $R_a$ and $R_b$, independently of the other, represents lower alkyl, for example methyl, or aryl, for example phenyl. Preferred compounds of trivalent phosphorus are tri-alkyl phosphites, for example trimethyl phosphite or triethyl phosphite.

The reaction is preferably carried out in an inert solvent, such as an aromatic hydrocarbon, for example benzene or toluene, an ether, for example dioxan or tetrahydrofuran, or a halogenated hydrocarbon, for example methylene chloride or chloroform, at a temperature of from approximately 20° to approximately 140° C., preferably at from approximately 20° to approximately 110° C., one molar equivalent of a compound of the formula III being reacted with two molar equivalents of the phosphorus compound Preferably, the compound of the formula III is placed in an inert solvent and the phosphorus compound, preferably dissolved in the same inert solvent, is added dropwise over a prolonged period, for example over a period of from 2 to 4 hours.

In a preferred embodiment of the process, the starting material of the formula III is manufactured in situ and, without being isolated from the reaction mixture, is reacted with the organic compound of trivalent phosphorus, the end products of the formula I being formed.

(c) Introduction of the Azaheterocyclyl Radical $R_3$

In compounds of the formula (IV) reactive esterified hydroxy Q represents, for example, hydroxy esterified by a hydrohalic acid, an organic sulphonic acid, such as a lower alkanesulphonic or optionally substituted benzenesulphonic acid, a lower alkanecarboxylic acid or a phosphinic acid and is especially halogen, for example chlorine, bromine or iodine, sulphonyloxy, for example methane-, benzene-, 4-toluene- or 4-bromobenzene-sulphonyloxy, lower alkanoyloxy, for example acetoxy, or phosphinoyloxy, for example dimethyl- or diphenylphosphinoyloxy.

An agent that introduces the azaheterocyclyl radical $R_3$ is especially a compound of the formula $R_3$—H in which the ring nitrogen atom to be linked to the radical -A- carries a hydrogen atom.

The reaction is carried out, for example, in the presence of a basic condensation agent, for example an alkali metal or alkaline earth metal hydroxide or carbonate, for example sodium hydroxide, sodium carbonate, potassium hydroxide, potassium carbonate or calcium carbonate, an alkali metal lower alkoxide, for example sodium methoxide, sodium ethoxide or potassium tert.-butoxide, an aromatic amine, for example pyridine or quinoline, or a tertiary aliphatic amine, such as a tri-lower alkylamine, for example triethylamine or di-isopropylethylamine, in an inert solvent, such as a lower alkanol, for example methanol or tert.-butanol, an amide, for example dimethylformamide, or, using a liquid amine as basic condensation agent, in excess amine at room temperature or at elevated or reduced temperature, for example at from approximately —20° to approximately +80° C.

It is preferable to use those starting materials of the formula II, III, and IV which result in the compounds of the formula I or I' mentioned at the beginning as being especially preferred, especially compounds of the formulae II and III that have a 3S,4R-configuration, or of the formula IV that have a 5R,6S-configuration.

In a resulting compound of the formula I or I' in which one or more functional groups are protected, these groups, for example protected amino, carboxy, hydroxy and/or sulpho groups, may be freed, optionally in stages or simultaneously, in a manner known per se by means of solvolysis, especially hydrolysis, alcoholysis or acidolysis, or by means of reduction, especially hydrogenolysis or chemical reduction.

In a compound of the formula I or I' obtainable according to the invention having a protected amino group, this group may be converted into the free amino group in a manner known per se, for example, depending on the nature of the protecting group, preferably by means of solvolysis or reduction. For example, 2-halo-lower alkoxycarbonylamino (optionally after converting a 2-bromo-lower alkoxycarbonylamino group into a 2-iodo-lower alkoxycarbonylamino group), aroylmethoxycarbonylamino or 4-nitrobenzyloxycarbonylamino can be cleaved by treatment with a suitable chemical reducing agent, such as zinc in the presence of a suitable carboxylic acid, such as aqueous acetic acid, or by catalysis with hydrogen in the presence of a palladium catalyst. Aroylmethoxycarbonylamino may be cleaved also by treatment with a nucleophilic, preferably salt-forming reagent, such as sodium thiophenolate, and 4-nitrobenzyloxycarbonylamino may be cleaved also by treatment with an alkali metal dithionite, for example sodium dithionite. Optionally substituted benzyloxycarbonylamino may be cleaved, for example, by means of hydrogenolysis, that is to say by treatment with hydrogen in the presence of a suitable hydrogenation catalyst, such as a palladium catalyst, and allyloxycarbonylamino by reaction with a palladium compound, for example tetrakis(triphenylphosphine)palladium, in the presence of triphenylphosphine and of an allyl group acceptor, for example 2-ethylhexanoic acid or a salt thereof. An amino group protected by an organic silyl or stannyl group can be freed, for example, by means of hydrolysis or alcoholysis, and an amino group protected by 2-halo-lower alkanoyl, for example 2-chloroacetyl, can be freed by treatment with thiourea in the presence of a base or with a thiolate salt, such as an alkali metal thiolate, of thiourea and subsequent solvolysis, such as alcoholysis or hydrolysis, of the resulting condensation product. An amino group protected by 2-substituted silylethoxycarbonyl can be converted into the free amino group by treatment with a salt of hydrofluoric acid that yields fluoride anions, such as an alkali metal fluoride, for example sodium fluoride, in the presence of a macrocyclic polyether ("Crown ether") or with a fluoride of an organic quaternary base, such as tetra-lower alkylammonium fluoride, for example tetraethylammonium fluoride. An amino group protected in the form of an azido or nitro group is converted into free amino, for example by reduction, for example by catalytic hydrogenation with hydrogen in the presence of a hydrogenation catalyst, such as platinum oxide, palladium or Raney nickel, or by treatment with zinc in the presence of an acid, such as acetic acid. An amino group protected in the form of a phthalimido group can be converted into the free amino group by reaction with hydrazine. Furthermore, an arylthioamino group can be converted into amino by treatment with a nucleophilic reagent, such as sulphurous acid.

In a compound of the formula I or I' obtainable according to the process in which $R_2$ represents a protected carboxy group and/or in which the radical $R_3$ or $R_3'$ contains protected carboxy as substituent, the carboxy group can be freed in a manner known per se. Thus, tert.-lower alkoxycarbonyl, or lower alkoxycarbonyl substituted in the 2-position by a tri-substituted silyl group or in the 1-position by lower alkoxy, or optionally substituted diphenylmethoxycarbonyl can be converted into free carboxy, for example, by treatment with a carboxylic acid, such as formic acid or trifluoroacetic acid, optionally with the addition of a nucleophilic compound, such as phenol or anisole. Optionally substituted benzyloxycarbonyl can be cleaved, for example, by means of hydrogenolysis, that is to say by treatment with hydrogen in the presence of a metallic hydrogenation catalyst, such as a palladium catalyst. Furthermore, suitably substituted benzyloxycarbonyl, such as 4-nitrobenzyloxycarbonyl, can also be converted into free carboxy by means of chemical reduction, for example by treatment with an alkali metal dithionite, for example sodium dithionite, or with a reducing metal, for example tin, or a reducing metal salt, such as a chromium(II) salt, for example chromium(II) chloride, customarily in the presence of a hydrogen-yielding agent that together with the metal is capable of producing nascent hydrogen, such as a suitable carboxylic acid, for example a lower alkanecarboxylic acid optionally substituted, for example, by hydroxy, for example acetic acid, formic acid or glycolic acid, or an alcohol or thiol, it being preferable to add water. The removal of an allyl protecting group can be effected, for example, by reaction with a palladium compound, for example tetrakis(triphenylphosphine)palladium, in the presence of triphenylphosphine and of an allyl group acceptor, for example 2-ethylhexanoic acid or a salt thereof. By treatment with a reducing metal or metal salt, as described above, it is also possible to convert 2-halo-lower alkoxycarbonyl (optionally after converting a 2-bromo-lower alkoxycarbonyl group into a corresponding 2-iodo-lower alkoxycarbonyl group) or aroylmethoxycarbonyl into free carboxy, it being possible to cleave aroylmethoxycarbonyl likewise by treatment with a nucleophilic, preferably salt-forming reagent, such as sodium thiophenolate or sodium iodide. Substituted 2-silylethoxycarbonyl can be converted into free carboxy also by treatment with a salt of hydrofluoric acid that yields the fluoride anion, such as an alkali metal fluoride, for example sodium fluoride, in the presence of a macrocyclic polyether ("Crown ether") or with a fluoride of an organic quaternary base, such as tetra-lower alkylammonium fluoride, for example tetrabutylammonium fluoride. Carboxy esterified by an organic silyl or stannyl group, such as tri-lower alkylsilyl or tri-lower alkylstannyl, can be freed in customary manner by solvolysis, for example by treatment with water or an alcohol. A lower alkoxycarbonyl group substituted in the 2-position by lower alkylsulphonyl or cyano can be converted into free carboxy, for example, by treatment with a basic agent, such as an alkali metal or alkaline earth metal hydroxide or carbonate, for example sodium or potassium hydroxide or sodium or potassium carbonate In compounds of the formula I or I' obtainable according to the process in which $R_1'$ is protected hydroxy, or the radical $R_1$ is substituted by protected hydroxy and/or in which the radical $R_3$ or $R_3'$ contains protected hydroxy as substituent, the protected hydroxy group can be converted into the free hydroxy group in a manner known per se. For example, a hydroxy group protected by a suitable acyl group or by an organic silyl or stannyl group is freed in the same manner as a correspondingly protected amino group: for example a tri-lower alkylsilyl group may be removed with tetrabutylammonium fluoride and acetic acid (under these conditions, carboxy groups protected by tri-substituted silylethoxy are not cleaved) A 2-halo-lower alkyl group and an optionally substituted benzyl group are removed by reduction A protected, especially esterified, sulpho group is freed in analogous manner to a protected carboxy group.

On the other hand, also compounds of the formula I or I' in which $R_2$ represents carboxy can be converted into compounds of the formula I or I' in which $R_2$ represents a protected carboxy group, especially an esterified carboxy group, or an esterified carboxy group that can be cleaved under physiological conditions. Thus, the free carboxy group can be esterified, for example, by treatment with a suitable diazo compound, such as a diazo-lower alkane, for example diazomethane, or a phenyldiazo-lower alkane, for example diphenyldiazomethane, if necessary in the presence of a Lewis acid, such as, for example, boron trifluoride, or by reaction with an alcohol suitable for esterification in the presence of an esterifying agent, such as a carbodiimide, for example dicyclohexyl carbodiimide, and carbonyldiimidazole. Esters can also be manufactured by reaction of a salt of the acid, which salt is optionally produced in situ, with a reactive ester of an alcohol and a strong inorganic acid, such as sulphuric acid, or a strong organic sulphonic acid, such as 4-toluenesulphonic acid. Furthermore, acid halides, such as chlorides (manufactured, for example, by treatment with oxalyl chloride), activated esters (formed, for example, with N-hydroxynitrogen compounds, such as N-hydroxysuccinimide), or mixed anhydrides (obtained, for example, with haloformic acid lower alkyl esters, such as chloroformic acid ethyl ester or chloroformic acid isobutyl ester, or with haloacetic acid halides, such as trichloroacetyl chloride) can be converted into an esterified carboxy group by reaction with suitable alcohols, optionally in the presence of a base, such as pyridine.

In a compound of the formula I or I' having an esterified carboxy group, this group can be converted into a different esterified carboxy group, for example 2-chloroethoxycarbonyl or 2-bromoethoxycarbonyl may be converted by treatment with an iodine salt, for example sodium iodide, into 2-iodoethoxycarbonyl. Furthermore, in compounds of the formula I or I' that contain a carboxy group $R_2'$ protected in esterified form, the carboxy-protecting group can be removed as described above, and a resulting compound of the formula I or I' having a free carboxy group or a salt thereof can be converted by reaction with the reactive ester of a corresponding alcohol into a compound of the formula I or I' in which $R_2$ represents an esterified carboxy group that can be cleaved under physiological conditions.

In compounds of the formula I or I', in addition, a radical $R_3$ or $R_3'$ can be converted into a different radical $R_3$ or $R_3'$.

Thus, for example, in compounds of the formula I or I' in which the heterocyclyl radical $R_3$ or $R_3'$ is substituted by a carboxy group, this carboxy group can be converted according to processes known per se into a functionally modified carboxy group, such as into an esterified carboxy group or into optionally substituted carbamoyl. For example, by reacting a compound of the formula I or I' in which $R_3$ or $R_3'$ represents heterocyclyl substituted by carboxy with an alcohol, especially a lower alkanol, there is obtained a compound of formula I or I' in which $R_3$ or $R_3'$ represents heterocyclyl substituted by esterified carboxy, especially lower alkoxycarbonyl, it being preferable to carry out the operation in the presence of a suitable condensation agent, for example a carbodiimide, or to remove the water formed by azeotropic distillation. On the other hand, carboxy groups in radicals $R_3$ or $R_3'$ can also be converted into reactive functional derivatives, such as mixed anhydrides, for example acid halides, or activated esters, and these can be converted by reaction with an alcohol, for example lower alkanol, ammonia or a primary or secondary amine, for example a lower alkylamine or di-lower alkylamine, into correspondingly esterified or amidated carboxy groups, it being preferable when using mixed anhydrides to carry out the operation in the presence of an acid-binding agent, such as an aromatic or tertiary amine or an alkali metal or alkaline earth metal carbonate.

If a heteroaryl radical $R_3$ or $R_3'$ contains a hydroxy group, this group may be etherified in customary manner. The reaction to form the corresponding lower alkyl-heteroaryl ethers is effected, for example, in the presence of bases, such as alkali metal hydroxides or carbonates, for example sodium hydroxide or potassium carbonate, with the aid of di-lower alkyl sulphates or lower alkyl halides, or with diazo-lower alkanes, or, in the presence of a dehydrating agent, for example dicyclohexyl carbodiimide, with the aid of lower alkanols. Furthermore, hydroxy may be converted into esterified hydroxy, for example lower alkanoyloxy, for example by reaction with the reactive derivative of a corresponding lower alkanecarboxylic acid, for example acetic acid, such as an anhydride thereof, for example the symmetric anhydride thereof, or a mixed anhydride with a hydrohalic acid, if necessary in the presence of a basic condensation agent, such as an alkali metal hydroxide or carbonate, or a nitrogen base, for example pyridine. The conversion of lower alkanoyloxy into hydroxy is effected, for example, by alcoholysis or, preferably, hydrolysis, for example by base-catalysed hydrolysis, for example in the presence of sodium hydroxide.

In compounds of the formula I in which $R_3$ or $R_3'$ represents heterocyclyl substituted by amino, the amino group may be converted into a substituted amino group, such as a lower alkylamino, di-lower alkylamino, lower alkyleneamino or lower alkanoylamino group. The conversion into a lower alkylamino or di-lower alkylamino group is effected, for example, by reaction with a reactive esterified lower alkanol, for example with a lower alkyl halide or sulphonate, in the presence of a basic condensation agent, such as a hydroxide or carbonate of an alkali metal or alkaline earth metal, or a heteroaromatic nitrogen base, for example pyridine. In analogous manner, amino can be converted by treatment with a lower alkylene dihalide or disulphonate into lower alkyleneamino, and by treatment with the reactive functional derivative of a lower alkanecarboxylic acid, for example the corresponding carboxylic acid halide, into lower alkanoylamino.

Salts of compounds of the formula I or I' having salt-forming groups may be manufactured in a manner known per se. Thus, salts of compounds of the formula I having a free carboxy group can be formed, for example, by treatment with metal compounds, such as alkali metal salts of suitable organic carboxylic acids, for example the sodium salt of α-ethylcaproic acid, or with inorganic alkali metal or alkaline earth metal salts, for example sodium bicarbonate, or with ammonia or with a suitable organic amine, it being preferable to use stoichiometric amounts or only a small excess of the salt-forming agent. Acid addition salts of compounds of the formula I or I' are obtained in customary manner, for example by treatment with a suitable acid or a suitable anion exchange reagent Internal salts of compounds of the formula I or I' can be formed, for example, by neutralising salts, such as acid addition salts, to the isoelectric point, for example with weak bases, or by treatment with ion exchangers.

Salts can be converted into the free compounds in customary manner; metal and ammonium salts, for example by treatment with suitable acids, and acid addition salts, for example by treatment with a suitable basic agent.

Resulting mixtures of isomers can be separated into the individual isomers according to methods known per se; mixtures of diastereoisomeric isomers, for example by fractional crystallisation, adsorption chromatography (column or thin-layer chromatography) or other suitable separating processes The cleaving of resulting racemates into their optical antipodes can be effected in various ways.

One of these ways comprises allowing a racemate to react with an optically active auxiliary, separating the resulting mixture of two diastereoisomeric compounds with the aid of suitable physico-chemical methods and then cleaving the individual diastereoisomeric compounds into the optically active compounds.

Racemates that are especially suitable for separation into the antipodes are those which contain an acidic group, such as, for example, racemates of compounds of the formula I in which $R_2$ represents carboxy. These acidic racemates can be reacted with optically active bases, for example esters of optically active amino acids, or (−)-brucine, (+)-quinidine, (−)-quinine, (+)-cinchonine, (+)-dehydroabietylamine, (+)- and (−)-ephedrin, (+)- and (−)-1-phenylethylamine or their N-mono- or N,N-di-alkylated derivatives, to form mixtures consisting of two diastereoisomeric salts.

In racemates that contain carboxy groups, this carboxy group can also be esterified already or can become esterified by an optically active alcohol, such as (−)-menthol, (+)-borneol, (+)- or (−)-2-octanol, whereupon, when isolation of the desired diastereoisomer is complete, the carboxy group is freed.

For separation of the racemates, the hydroxy group can also be esterified by optically active acids or reactive functional derivatives thereof, diastereoisomeric esters being formed. Such acids are, for example, (−)-abietic acid, D(+)- and L(−)-malic acid, N-acylated optically active amino acid, (+)- and (−)-camphanic acid, (+)- and (−)-ketopinic acid, L(+)-ascorbic acid, (+)-camphoric acid, (+)-camphor-10-sulphonic acid(8), (+)- or (−)-α-bromocamphor-π-sulphonic acid, D(−)-quinic acid, D(−)-isoascorbic acid, D(−)- and L(+)-mandelic acid, (+)-1-menthoxyacetic acid, D(−)- and L(+)-tartaric acid and the di-O-benzoyl and di-O-p-toluyl derivatives thereof By reaction with optically active isocyanates, such as with (+)- or (−)-1-phenylethyl isocyanate, it is possible to convert compounds of the formula I in which $R_2$ represents protected carboxy and the radical $R_1$ represents lower alkyl substituted by hydroxy into a mixture of diastereoisomeric urethanes.

Basic racemates, for example compounds of the formula I in which the radical $R_3$ is substituted by amino, can form diastereoisomeric salts with the mentioned optically active acids.

The cleaving of the separated diastereoisomers into the optically active compounds of the formula I is also effected according to customary methods. The acids or the bases are freed from the salts, for example by treatment with acids or bases that are stronger than those originally used. The desired optically active compounds are obtained from the esters and urethanes, for example, after alkaline hydrolysis or after reduction with a complex hydride, such as lithium aluminium hydride.

A further method of separating the racemates comprises chromatography on optically active absorption layers, for example on cane sugar.

According to a third method, the racemates can be dissolved in optically active solvents and the more sparingly soluble optical antipode can be crystallised out.

A fourth method utilises the different reactivities of the optical antipodes with respect to biological material, such as micro-organisms or isolated enzymes.

According to a fifth method, the racemates are dissolved and one of the optical antipodes is crystallised out by inoculation with a small quantity of an optically active product obtained according to one of the above methods The separation of diastereoisomers into the individual racemates and of the racemates into the optical antipodes can be carried out at any stage of the process, that is to say, for example, even at the stage of the starting compounds of the formulae II to IV or at any stage of the process for the manufacture of the starting material of the formula II or IV that is described hereinafter.

In all subsequent conversions of resulting compounds of the formula I or I', those reactions are preferred which take place under neutral or alkaline, especially weakly alkaline, conditions.

The process also includes those embodiments according to which compounds formed as intermediates are used as starting materials and the remaining process steps are carried out with them, or the process is discontinued at any stage. Furthermore, starting materials can be used in the form of derivatives or can be formed in situ, optionally under the reaction conditions. For example, a starting material of the formula II in which Z represents oxygen can be manufactured in situ from a compound of the formula II in which Z represents an optionally substituted methylidene group, as described hereinafter, by ozonisation and subsequent reduction of the ozonide formed, analogously to the process (Stage 2.3) described hereinafter, whereafter the cyclisation to form the compound of the formula I is effected in the reaction solution.

The starting compounds of the formulae II, III and IV and the precursors can be manufactured as indicated in reaction schemes I, II and III.

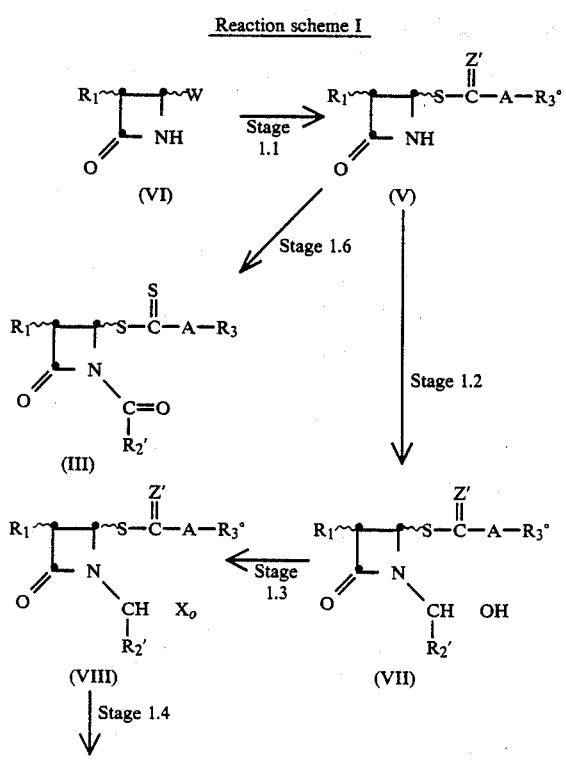

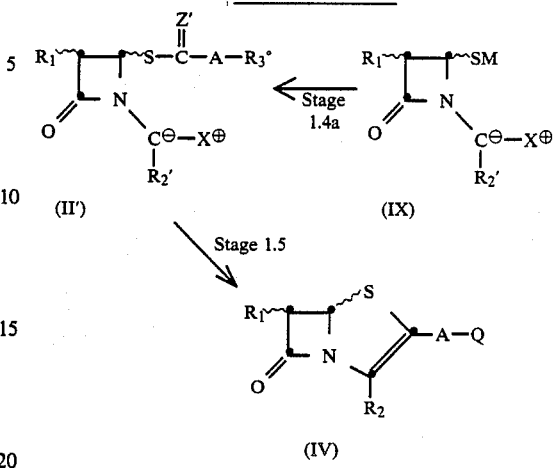

Reaction scheme I

In the compounds of the formulae V, VII, VIII and II', Z' represents oxygen, sulphur or alternatively a methylidene group that is optionally substituted by one or two substituents Y and can be converted by oxidation into an oxo group Z. A substituent Y of this methylidene group is an organic radical, for example optionally substituted lower alkyl, for example methyl or ethyl, cycloalkyl, for example cyclopentyl or cyclohexyl, phenyl or phenyl-lower alkyl, for example benzyl, or, especially, an esterified carboxy group, including a carboxy group esterified by an optically active alcohol, such as 1-menthol, for example one of the optionally substituted lower alkoxycarbonyl or arylmethoxycarbonyl radicals mentioned under $R_2$ or alternatively 1-menthyloxycarbonyl. The methylidene group Z' preferably carries one of the mentioned substituents. Special mention should be made of the methoxycarbonylmethylidene, ethoxycarbonylmethylidene and the 1-menthyloxycarbonylmethylidene group Z'. The latter can be used for the manufacture of optically active compounds of the formulae V, VII, VIII and II'.

In the compounds of the formulae V, VII, VIII and II', $R_3°$ represents either the radical $R_3$ or a reactive esterified hydroxy group Q.

In the compounds of the formulae V to IX and II', the radical $R_1$ preferably contains one of the mentioned protected hydroxy groups, for example optionally substituted 1-phenyl-lower alkoxy, optionally substituted phenyl-lower alkoxycarbonyloxy, or trisubstituted silyloxy.

Stage 1.1

A thioazetidinone of the formula V is obtained by treating a 4-W-azetidinone of the formula VI in which W represents a nucleofugal leaving group with a mercapto compound of the formula $$R_3°—A—C(=Z')—SH$$

or with a salt, for example an alkali metal salt, such as a sodium or potassium salt, thereof, and, if desired, in a resulting compound of the formula V, in which the radical $R_1$ is substituted by hydroxy, converting hydroxy into protected hydroxy.

The nucleofugal leaving group W in a starting material of the formula VI is a radical that can be replaced by the nucleophilic radical $R_3°—A—C(=Z')—S—$.

Such groups W are, for example, acyloxy radicals, sulphonyl radicals $R_0—SO_2—$ in which $R_0$ is an organic radical, or azido or halogen. In an acyloxy radical W, acyl is, for example, the radical of an organic carboxylic acid, including an optically active carboxylic acid, and represents, for example, lower alkanoyl, for example acetyl or propionyl, optionally substituted benzoyl, for example benzoyl or 2,4-dinitrobenzoyl, phenyl-lower alkanoyl, for example phenylacetyl, or the acyl radical of one of the above-mentioned optically active acids. In a sulphonyl radical $R_0—SO_2—$, $R_0$ is, for example, lower alkyl optionally substituted by hydroxy, such as methyl, ethyl or 2-hydroxyethyl, and also correspondingly substituted optically active lower alkyl, for example (2R)- or (2S)-1-hydroxyprop-2-yl, methyl substituted by an optically active radical, such as camphoryl, or benzyl, or optionally substituted phenyl, such as phenyl, 4-bromophenyl or 4-methylphenyl. A halogen radical W is, for example, bromine, iodine or, especially, chlorine W is preferably methyl- or 2-hydroxyethyl-sulphonyl, acetoxy or chlorine.

The nucleophilic substitution can be carried out under neutral or weakly basic conditions in the presence of water and, optionally, a water-miscible organic solvent. The basic conditions can be produced, for example, by the addition of an inorganic base, such as an alkali metal or alkaline earth metal hydroxide, carbonate or bicarbonate, for example sodium, potassium or calcium hydroxide, carbonate or bicarbonate. As organic solvents there may be used, for example, water-miscible alcohols, for example lower alkanols, such as methanol or ethanol, ketones, for example lower alkanones, such as acetone, amides, for example lower alkanecarboxylic acid amides, such as dimethylformamide, acetonitrile and the like. The reaction is customarily carried out at room temperature but may also be carried out at elevated or reduced temperature. The reaction can be accelerated by the addition of a salt of hydriodic acid or of thiocyanic acid, for example an alkali metal salt, such as a sodium salt.

It is possible to use in the reaction optically inactive cis- or trans-compounds of the formula VI and mixtures thereof, or corresponding optically active compounds. The group being introduced, $R_3°—A—C(=Z')—S—$, is directed by the group $R_1$ preferentially into the trans-position, irrespective of whether W is in the cis-or trans-position to the group $R_1$. Although predominantly the trans-isomers are formed, it is occasionally possible also to isolate the cis-isomers. The separation of the cis- and trans-isomers is effected as described above, according to conventional methods, especially by chromatography and/or by crystallisation.

The subsequent ozonisation of a methylidene group Z' can be effected as described hereinafter. A resulting racemate of the formula V can be separated into the optically active compounds.

An azetidinone of the formula VI in which $R_1$ represents acetoxymethyl is described in German Offenlegungsschrift No. 29 50 898.

Other azetidinones of the formula VI can be manufactured according to processes known per se, for example by reacting a vinyl ester of the formula $R_1—CH=CH—W$ with chlorosulphonyl isocyanate and reacting the resulting cyclo adduct with a reducing agent, for example sodium sulphite. In this synthesis, mixtures of cis-and trans-isomers are customarily obtained which, if desired, can be separated into the pure cis- or trans-isomers, for example by chromatography and/or crystallisation or distillation. The pure cis- and trans-isomers are in the form of racemates and can be separated into their optical antipodes, for example if acyl in an acyloxy radical W in compounds of the formula VI originates from an optically active acid. The compounds of the formula VI, especially their optically active forms, can also be manufactured according to the process given in reaction scheme II.

Stage 1.2

An α-hydroxycarboxylic acid compound of the formula VIII is obtained by reacting a compound of the formula V with a glyoxylic acid compound of the formula $OHC—R_2'$ or with a suitable derivative thereof, such as a hydrate, hemihydrate or semiacetal, for example a semiacetal with a lower alkanol, for example methanol or ethanol, and, if desired, in a resulting compound of the formula VII in which the radical $R_1$ is substituted by hydroxy, converting hydroxy into protected hydroxy.

The compound of the formula VII is customarily obtained in the form of a mixture of the two isomers (with respect to the >CH~OH grouping). It is also possible, however, to isolate the pure isomers thereof.

The addition of the glyoxylic acid ester compound to the nitrogen atom of the lactam ring is effected at room temperature or, if necessary, while heating, for example up to approximately 100° C., and in the absence of a true condensation agent and/or without formation of a salt. When using the hydrate of the glyoxylic acid compound, water is formed which, if necessary, is removed by distillation, for example azeotropically, or by using a suitable dehydrating agent, such as a molecular sieve. It is preferable to carry out the operation in the presence of a suitable solvent, such as, for example, dioxan, toluene or dimethylformamide, or a solvent mixture, if desired or necessary in the atmosphere of an inert gas, such as nitrogen.

It is possible to use in the reaction pure optically inactive cis- or trans-compounds of the . formula V and mixtures thereof, or corresponding optically active compounds. A resulting racemate of the formula VII can be separated into the optically active compounds.

Stage 1.3

Compounds of the formula VIII in which $X_0$ represents a reactive esterified hydroxy group, especially halogen or organic sulphonyloxy, are manufactured by, in a compound of the formula VII, converting the secondary hydroxy group into a reactive esterified hydroxy group, especially into halogen, for example chlorine or bromine, or into an organic sulphonyloxy group, such as lower alkanesulphonyloxy, for example methanesulphonyloxy, or arenesulphonyloxy, for example benzene- or 4-methylbenzene-sulphonyloxy.

In the starting compounds of the formula VII, $R_1$ preferably represents lower alkyl substituted by a protected hydroxy group.

The compounds of the formula VIII can be obtained in the form of mixtures of the isomers (with respect to the >CH~$X_0$ grouping) or in the form of pure isomers.

The above reaction is carried out by treatment with a suitable esterifying agent, for example with a thionyl halide, for example the chloride, a phosphorus oxyhalide, especially the oxychloride, a halophosphonium halide, such as triphenyl phosphono-dibromide or -diiodide, or a suitable organic sulphonic acid halide, such as the chloride, preferably in the presence of a basic agent, especially an organic basic agent, such as an aliphatic tertiary amine, for example triethylamine, diisopropylethylamine or "polystyrene Hünig base" or a heterocyclic base of the pyridine type, for example pyridine or collidine. The operation is preferably carried out in the presence of a suitable solvent, for example dioxan or tetrahydrofuran, or a solvent mixture, if necessary while cooling and/or in the atmosphere of an inert gas, such as nitrogen.

In a compound of the formula VIII obtainable in this manner, a reactive esterified hydroxy group $X_0$ can be converted into a different reactive esterified hydroxy group in a manner known per se. Thus, for example, a chlorine atom can be replaced by a bromine or iodine atom by treatment of the corresponding chlorine compound with a suitable bromide or iodide salt, such as lithium bromide or iodide, preferably in the presence of a suitable solvent, such as ether.

It is possible to use in the reaction pure optically inactive cis- or trans-compounds of the formula VII and mixtures thereof, or corresponding optically active compounds. A resulting racemate of the formula VIII can be separated into the optically active compounds.

Stage 1.4

The starting material of the formula II' is obtained by treating a compound of the formula VIII in which $X_0$ represents a reactive esterified hydroxy group with a suitable phosphine compound, such as a tri-lower alkylphosphine, for example tri-n-butylphosphine, or a triarylphosphine, for example triphenylphosphine, or with a suitable phosphite compound, such as a tri-lower alkyl phosphite, for example triethyl phosphite, or an alkali metal di-lower alkyl phosphite, for example diethyl phosphite.

The above reaction is preferably carried out in the presence of a suitable inert solvent, such as a hydrocarbon, for example hexane, cyclohexane, benzene, toluene or xylene, or an ether, for example dioxan, tetrahydrofuran or diethylene glycol dimethyl ether, or a solvent mixture. Depending upon reactivity, the operation is carried out while cooling or at elevated temperature, at approximately from $-10°$ to $+100°$ C., preferably at approximately from 20° to 80° C., and/or in the atmosphere of an inert gas, such as nitrogen. In order to prevent oxidative processes taking place catalytic amounts of an antioxidant, for example hydroquinone, can be added.

When using a phosphine compound, the operation is customarily carried out in the presence of a basic agent, such as an organic base, for example an amine, such as triethylamine, diisopropylethylamine or "polystyrene Hünig base", and there is thus obtained directly the ylide starting material of the formula II (or II') which is formed from the corresponding phosphonium salt.

A starting compound of the formula II in which $X^\oplus$ represents a phosphono group together with a cation is preferably manufactured in situ by treating a resulting compound of the formula

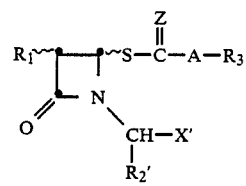

(IIa)

in which $X^1$ represents a phosphono group with a suitable basic reagent, such as an inorganic base, for example an alkali metal carbonate, such as sodium or potassium carbonate, or an organic base, such as a tri-lower alkylamine, for example triethylamine, or a cyclic base of the amidine type, such as a corresponding diazabicycloalkene compound, for example 1,5-diazabicyclo[5.4.0]undec-5-ene.

It is possible to use in the reaction pure, optically inactive cis- or trans-compounds of the formula VIII and mixtures thereof, or corresponding optically active compounds. A resulting racemate of the formula II' can be separated into the optically active compounds.

Stage 1.4a

A starting compound of the formula II' in which $Z'$ represents oxo can furthermore be obtained by treating a mercaptide of the formula IX, in which M represents a metal cation, with an acylating agent that introduces the radical $R_3°—A—C(=O)—$.

In the starting material of the formula IX, the metal cation M is, for example, a cation of the formula $M^+$ or $M^{2+}/2$, in which $M^+$ represents especially a silver cation and $M^{2+}$ represents especially the divalent cation of a suitable transition metal, for example copper, lead or mercury.

An acylating agent that introduces the radical $R_3°—A—C(=O)—$ is, for example, the acid $R_3°—A—COOH$ or a reactive functional derivative thereof, such as an acid halide, for example chloride or bromide, or an azide or anhydride thereof.

If the free acid of the formula $R_3°—A—COOH$ is used, the acylation is carried out, for example, in the presence of a suitable water-removing agent, such as a carbodiimide, for example N,N'-dicyclohexyl carbodiimide, or, if an acid derivative is used, it is carried out in the presence of a suitable acid-binding agent, such as a tertiary aliphatic or aromatic base, for example triethylamine, pyridine or quinoline, in an inert solvent, such as a chlorinated hydrocarbon, for example methylene chloride, or an ether, for example diethyl ether or dioxan, at room temperature or while heating or cooling, for example in a temperature range of from approximately $-50°$ to approximately $+60°$ C., especially at from approximately $-30°$ to approximately $+20°$ C.

The starting compounds of the formula IX can be manufactured, for example, by converting an azetidinone of the formula

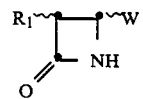

(VI)

by reaction with an alkali metal salt, for example the sodium salt, of a thio-lower alkanecarboxylic acid, for example thioacetic acid, or of a triphenylmethylmercaptan, into a compound of the formula

in which W' represents triphenylmethylthio or lower alkanoylthio, for example acetylthio, converting this, analogously to the process described in reaction stages 1.2, 1.3 and 1.4, into a compound of the formula

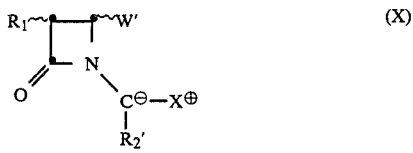

and reacting this, in the presence of a base, for example pyridine or tri-n-butylamino, in a suitable solvent, for example diethyl ether or methanol, with a salt of the formula MA, in which M has the meaning given above but represents especially a silver cation, and A represents a customary anion that favours the solubility of the salt MA in the chosen solvent, for example the nitrate, acetate or fluoride anion.

Compounds of the formula (II') in which $R_3°$ represents a reactive esterified hydroxy group can be converted by reaction with an agent that introduces the azaheterocyclyl radical $R_3$ into compounds of the formula (II') in which $R_3°$ represents the radical $R_3$, for example the reaction conditions given in process (c) being used.

The ylides of the formula II' in which Z' represents oxygen or sulphur can be used directly in the cyclisation reaction for the manufacture of the end products of the formula I. It is also possible, however, in compounds of the formula II' in which $R_1$ contains as substituent a protected hydroxy group, for example a protected hydroxy group that can readily be cleaved by hydrolysis, such as trisubstituted silyloxy, first to remove the hydroxy-protecting group and then to use the resulting compound of the formula II' in which $R_1$ represents lower alkyl substituted by hydroxy in the cyclisation reaction.

In the compounds of the formulae II', V, VII and VIII, an optionally substituted methylidene group Z' can be converted into the oxo group Z by ozonisation and subsequent reduction of the ozonide formed, according to the process described hereinafter in stage 2.3.

Stage 1.5

The starting compound of the formula (IV) is obtained by cyclising an ylide of the formula (II') in which Z' represents oxygen or sulphur and $R_3°$ represents a reactive esterified hydroxy group Q, and, optionally, converting a protected carboxy group $R_2'$ in a resulting compound into the free carboxy group $R_2$.

The cyclisation can be carried out, for example, in the same manner as is described for the manufacture of compounds of the formula (I) from the ylides of the formula (II) (process a).

The conversion of a protected carboxy group $R_2'$ into a free carboxy group $R_2$ in a resulting compound of the formula IV can be carried out in a manner analogous to that described hereinbefore for the compounds of the formula I.

Stage 1.6

A compound of the formula (III) is obtained by treating an azetidinone of the formula (V) in which Z' represents sulphur and $R_3'$ represents the radical $R_3$, with a compound of the formula $R_2'$—COOH or especially a reactive derivative, such as an acid halide, for example the acid chloride, thereof at a temperature of from 20° to 80° C., prefereably from 40° to 60° C., in an inert solvent, such as one of the solvents mentioned for the reaction of compounds of the formula III to form compounds of the formula I. When using an acid halide, the operation is preferably carried out in the presence of an acid-binding agent, such as a tertiary aliphatic amine, for example triethylamine, an aromatic amine, for example pyridine, or especially an alkali metal or alkaline earth metal carbonate or bicarbonate, for example potassium carbonate or calcium carbonate.

In an analogous manner starting materials for the preparation of the compounds of the formula I' can be prepared as follows:

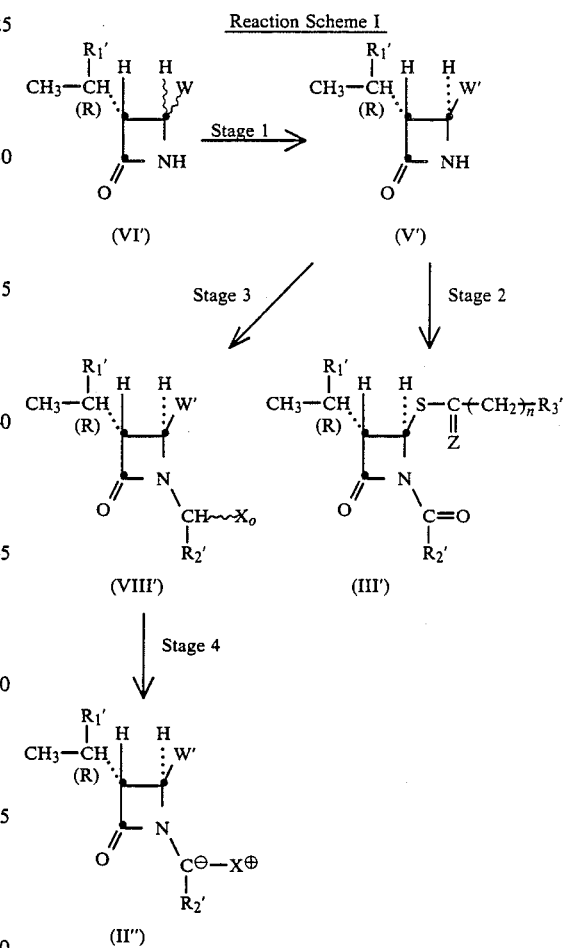

Reaction Scheme I

In the compounds of the formulae V', VIII' and II'', W' represents the radical —S—C(=Z)—(CH$_2$)$_m$—R$_3$ or triphenylmethylthio or lower alkanoylthio. (5R,6S)-configured starting compounds of the formula VI in which W represents a sulphonyl radical of the formula $R_0$—SO$_2$— can also be manufactured according to the following reaction scheme II.

Reaction scheme II

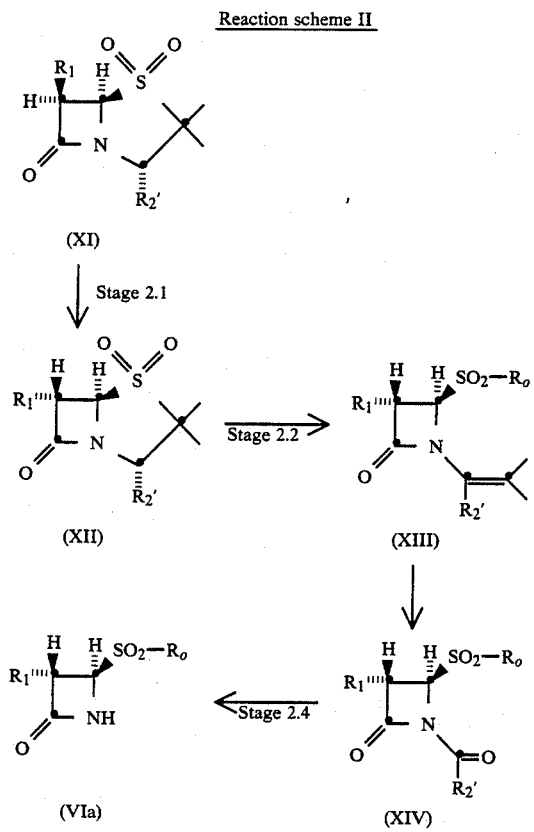

In the compounds of the formulae (XI) to (XIV) and (VIa) $R_1$ represents lower alkyl substituted by hydroxy, or especially lower alkyl substituted by a protected hydroxy group.

Stage 2.1

Compounds of the formula (XII) can be manufactured by epimerising a compound of the formula (XI).

The epimerisation is effected, for example, in the presence of a basic agent, such as an amine, for example a tri-lower alkylamine, for example triethylamine or ethyldiisopropylamine, a tertiary amine, for example N,N-dimethylaniline, an aromatic amine, for example pyridine, or a bicyclic amine, for example 1,5-diazabicyclo[5.4.0]undec-5-ene or 1,5-diazabicyclo[4.3.0]non-5-ene, or an alkali metal-lower alkoxide, for example sodium methoxide, sodium ethoxide or potassium tert.-butoxide, in an inert solvent, for example an ether, for example diethyl ether, dimethoxyethane, tetrahydrofuran or dioxan, acetonitrile or dimethylformamide, optionally at slightly elevated or reduced temperature, for example at from 0° to 50° C., but preferably at room temperature.

In the compounds of the formula (XII) obtainable according to the process, a protected hydroxy group contained in the radical $R_1$ can be replaced by a different protected hydroxy group; for example a protected hydroxy group that can be cleaved by hydrogenolysis can be replaced by a protected hydroxy group that can be cleaved by solvolysis. Hydroxy-protecting groups are especially those mentioned above; protecting groups that can be removed by hydrogenolysis are, for example, 1-phenyl-lower alkyl or phenyl-lower alkoxycarbonyl, each substituted as indicated, and protecting groups that can be removed by solvolysis are, for example, silyl tri-substituted as indicated.

The reaction can be carried out by first removing the hydroxy-protecting group that can be removed by hydrogenolysis and then introducing into the resulting compound of the formula XII in which $R_1$ represents lower alkyl substituted by hydroxy, a hydroxy-protecting group that can be removed by solvolysis.

The removal of the protecting group that can be removed by hydrogenolysis is effected, for example, with hydrogen or a hydrogen-donor, for example cyclohexene or cyclohexadiene, in the presence of a hydrogenation catalyst, such as a palladium catalyst, for example palladium-on-carbon, in an inert solvent, such as a halogenated hydrocarbon, for example methylene chloride, a lower alkanol, for example methanol or ethanol, an ether, for example dioxan or tetrahydrofuran, or alternatively in water or in mixtures thereof, at a temperature of from approximately 0° to approximately 80° C., preferably at room temperature. The removal can also be carried out with a reducing metal, such as zinc, or a reducing metal alloy, for example a copper-/zinc alloy, in the presence of an agent that yields protons, such as an organic acid, for example acetic acid, or alternatively a lower alkanol, for example ethanol.

The introduction of a hydroxy-protecting group that can be removed by solvolysis is effected, for example, with a compound of the formula $R'—X_3$ in which $R'$ represents the hydroxy-protecting group and $X_3$ represents, for example, a reactive esterified hydroxy group, for example halogen, for example chlorine, bromine or iodine, or sulphonyloxy, such as methanesulphonyloxy, benzenesulphonyloxy or 4-toluenesulphonyloxy.

Starting compounds of the formula (XI) are known, for example, from German Offenlegungsschrift No. 3 039 504 and from British Patent Application No. 20 61 930.

Stage 2.2

A compound of the formula (XIII) can be manufactured by treating a penam compound of the formula (XII) with a basic agent and with an esterifying agent that introduces the radical $R_0$.

A suitable basic agent is, for example, one of the basic agents mentioned under stage 2.1, especially one of the mentioned bicyclic amines, and also an alkali metal amide or hydride, for example sodium amide or sodium hydride.

A radical $R_0$ is, for example, one of the organic radicals mentioned under stage 1.1, especially optionally substituted lower alkyl, for example methyl, ethyl or 2-hydroxyethyl, or benzyl.

An esterifying agent that introduces the radical $R_0$ is, for example, a compound of the formula $R_0—X_4$ in which $X_4$ represents reactive esterified hydroxy, for example halogen, such as chlorine, bromine or iodine, or sulphonyloxy, such as methanesulphonyloxy, benzenesulphonyloxy or 4-toluenesulphonyloxy. For the introduction of a 2-hydroxyethyl radical, ethylene oxide is also suitable.

The reaction is preferably carried out in two steps; in the first step the penam compound of the formula (XII) is treated with at least equimolar amounts of the basic agent and a resulting intermediate of the formula

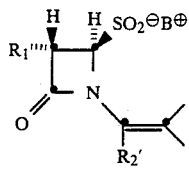

(XIIa)

in which B⊕ represents the protonated form (cation) of the basic agent, is reacted with the esterifying agent, preferably without being isolated from the reaction mixture. The reaction is carried out in an inert solvent, for example an ether, for example diethyl ether, dimethoxyethane, tetrahydrofuran or dioxan, in acetonitrile, dimethylformamide or hexamethylphosphoric acid triamide, optionally at slightly elevated or reduced temperature, for example at approximately from 0° to 50° C., but preferably at room temperature. In a preferred embodiment of the process, the penam compound of the formula (XII) is manufactured in situ by, as described in stage 2.1, first treating a compound of the formula (XI) with catalytic amounts of the basic agent, for example 1,5-diazabicyclo[5.4.0]-undec-5-ene, and then further reacting the product with at least equimolar amounts of the same basic agent and the esterifying agent to form the compounds of the formula (XIII).

Stage 2.3

An oxalylazetidinone of the formula (XIV) can be manufactured by ozonising a compound of the formula (XIII) and cleaving the ozonide formed by reduction to form the oxo compound.

The ozonisation is customarily carried out with a mixture of ozone and oxygen in an inert solvent, such as a lower alkanol, for example methanol or ethanol, a lower alkanone, for example acetone, an optionally halogenated hydrocarbon, for example a halo-lower alkane, such as methylene chloride or carbon tetrachloride, or in a solvent mixture, including an aqueous mixture, preferably while cooling, for example at temperatures of from approximately −80° to approximately 0° C.

An ozonide obtained as intermediate is cleaved by reduction, customarily without being isolated, to form a compound of the formula XIV, there being used catalytically activated hydrogen, for example hydrogen in the presence of a heavy metal hydrogenation catalyst, such as a nickel catalyst and also a palladium catalyst, preferably on a suitable carrier, such as calcium carbonate or carbon, or chemical reducing agents, such as reducing heavy metals, including heavy metal alloys or amalgams, for example zinc, in the presence of a hydrogen-donor, such as an acid, for example acetic acid, or an alcohol, for example lower alkanol, reducing inorganic salts, such as alkali metal iodides, for example sodium iodide, or alkali metal bisulphites, for example sodium bisulphite, in the presence of a hydrogen-donor, such as an acid, for example acetic acid, or water, or reducing organic compounds, such as formic acid. As reducing agents there may also be used compounds that can readily be converted into corresponding epoxide compounds or oxides, it being possible for the epoxide formation to be effected as a result of a C—C double bond and the oxide formation in view of the presence of an oxide-forming hetero atom, such as a sulphur, phosphorus or nitrogen atom. Such compounds are, for example, suitably substituted ethene compounds (which are converted into ethylene oxide compounds in the reaction), such as tetracyanoethylene; or, especially, suitable sulphide compounds (which are converted into sulphoxide compounds in the reaction), such as di-lower alkyl sulphides, especially dimethyl sulphide; suitable organic phosphorus compounds, such as a phosphine optionally substituted by phenyl and/or lower alkyl, for example methyl, ethyl, n-propyl or n-butyl (which phosphine is converted into a phosphine oxide in the reaction), such as tri-lower alkylphosphines, for example tri-n-butylphosphine, or triphenylphosphine; and also tri-lower alkyl phosphites (which are converted into phosphoric acid tri-lower alkyl esters in the reaction), customarily in the form of corresponding alcohol adduct compounds, such as trimethyl phosphite, or phosphorous acid triamides, which optionally contain lower alkyl as substituent, such as hexa-lower alkyl phosphorous acid triamides, for example hexamethylphosphorous acid triamide, the latter preferably being in the form of a methanol adduct; and also suitable nitrogen bases (which are converted into the corresponding N-oxides in the reaction), such as heterocyclic nitrogen bases of aromatic character, for example bases of the pyridine type and, especially, pyridine itself. The cleaving of the ozonide, which customarily is not isolated, is normally effected under the same conditions as those used for its manufacture, that is to say, in the presence of a suitable solvent or solvent mixture, and while cooling or heating gently, the operation preferably being carried out at temperatures of from approximately −10° to approximately +25° C., and the reaction customarily being concluded at room temperature.

Stage 2.4

An azetidinone of the formula (VIa) can be manufactured by solvolysing an oxalylazetidinone of the formula (XIV).

The solvolysis can be carried out in the form of hydrolysis, alcoholysis or alternatively in the form of hydrazinolysis. Hydrolysis is carried out with water, optionally in a water-miscible solvent. Alcoholysis is customarily carried out with a lower alkanol, for example methanol or ethanol, preferably in the presence of water and an organic solvent, such as a lower alkanecarboxylic acid lower alkyl ester, for example ethyl acetate, preferably at room temperature, if necessary while cooling or heating, for example at a temperature of from approximately 0° to approximately 80° C. Hydrazinolysis is carried out in conventional manner with a substituted hydrazine, for example with phenyl- or a nitrophenyl-hydrazine, such as 2-nitrophenylhydrazine, 4-nitrophenylhydrazine or 2,4-dinitrophenylhydrazine, which is preferably used in an approximately equimolar amount, in an organic solvent, such as an ether, for example diethyl ether, an aromatic hydrocarbon, such as benzene, a halogenated hydrocarbon, such as methylene chloride, an ester, such as ethyl acetate, and the like, at temperatures of from approximately room temperature to approximately 65° C.

In a preferred embodiment of the process, a compound of the formula (XIII) is used as starting material and is ozonised as indicated and then cleaved by reduction to form an oxalylazetidinone of the formula (XIV) which is reacted further, without being isolated from the reaction mixture, to form an azetidinone of the formula (VIa).

In the ozonolysis there may be produced small amounts of acid which can effect the removal of a hydroxy-protecting group R' in the radical $R_1$ that can readily be removed by solvolysis, for example a tri-substituted silyl radical. The resulting compound of the formula

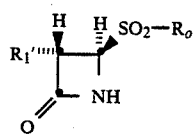

in which $R_1'$ represents lower alkyl substituted by hydroxy can be separated from the protected azetidinone (VIa), for example by chromatography, and converted into the azetidinone of the formula (VIa) by fresh reaction with the agent of the formula $R'—X_3$ that introduces the hydroxy-protecting group R'.

In the compounds of the formulae (II), (II'), (III), (IV), (VII) to (IX) and (XII) to (XIV), a protected carboxy group $R_2'$ can be converted into a different protected carboxy group $R_2'$ according to methods known per se, and when so doing it is possible, taking into consideration the other functional groups which may be contained in these compounds, to use the same methods as those indicated for the conversion of this substituent in the compounds of the formula (I).

The invention relates also to novel starting materials and to novel intermediates obtainable according to the process, such as those of the formulae (II) to (IX) (including II', II", IIa, III', VIa and VIII') and to the processes given for their manufacture.

The starting materials used and the reaction conditions chosen are preferably those which result in the compounds described hereinbefore as being especially preferred.

The compounds of the formula I and I' have valuable pharmacological properties, or can be used as intermediates for the manufacture of such compounds having valuable pharmacological properties. Compounds of the formula I in which $R_1$ represents lower alkyl substituted by hydroxy or $R_1'$ represents hydroxy, $R_2$ represents carboxy, or an esterified carboxy group that can be cleaved under physiological conditions, and $R_3$, $R_3'$, n and A have the meanings given under formula I or I', and pharmacologically acceptable salts of such compounds having salt-forming groups have anti-bacterial activity. For example, they are effective in vitro against gram-positive and gram-negative cocci, for example *Staphylococcus aureus, Streptococcus pyogenes, Streptococcus pneumoniae, Streptococcus faecalis, Neisseria meningitidis* and *Neisseria gonorrhoeae*, and against enterobacteria, for example *Escherichia coli* and *Proteus* sp., against *Haemophilus influenzae* and *Pseudomonas aerugnosa*, and anaerobes, for example *Bacteroides* sp., in minimum concentrations of from approximately 0.01 to approximately 64 µg/ml. In vivo, in the case of systemic infection of mice, for example by *Staphylococcus aureus, Escherichia coli* or *Streptococcus pyogenes*, on subcutaneous or oral administration $ED_{50}$ values of from approximately 1 to approximately 70 mg/kg result.

The novel compounds can be used as orally or parenterally administrable antibacterial antibiotics, for example in the form of corresponding pharmaceutical preparations, for the treatment of infections.

Compounds of the formula I or I' in which at least one of the functional groups present is in protected form, a protected carboxy group being other than an esterified carboxy group that can be cleaved under physiological conditions, can be used as intermediates for the manufacture of the above-mentioned pharmacologically active compounds of the formula I or I'.

The pharmacologically acceptable compounds of the present invention can be used, for example, for the manufacture of pharmaceutical preparations that contain a therapeutically effective amount of the active ingredient together or in admixture with inorganic or organic, solid or liquid, pharmaceutically acceptable carriers that are suitable for oral or for parenteral, that is to say intramuscular, subcutaneous or intraperitoneal, administration.

For oral administration there are used tablets or gelatine capsules that contain the active ingredient together with diluents, for example lactose, dextrose, sucrose, mannitol, sorbitol, cellulose and/or glycine, and lubricants, for example silica, talc, stearic acid or salts thereof, such as magnesium or calcium stearate, and/or polyethylene glycol; tablets also contain binders, for example magnesium aluminium silicate, starches, such as corn, wheat, rice or arrowroot starch, gelatine, tragacanth, methylcellulose, sodium carboxymethylcellulose and/or polyvinylpyrrolidone, and, if desired, disintegrators, for example starches, agar, alginic acid or a salt thereof, such as sodium alginate, and/or effervescent mixtures or adsorbents, colourings, flavourings or sweeteners.

For parenteral administration there are suitable especially infusion solutions, preferably isotonic aqueous solutions or suspensions, it being possible to prepare these before use, for example from lyophilised preparations that contain the active ingredient alone or together with a carrier, for example mannitol. Such preparations may be sterilised and/or contain adjuncts, for example preservatives, stabilisers, wetting agents and/or emulsifiers, solubilisers, salts for regulating the osmotic pressure and/or buffers.

The present pharmaceutical preparations, which, if desired, may contain other pharmacologically valuable substances, are manufactured in a manner known per se, for example by means of conventional mixing, dissolving or lyophilising processes, and contain from approximately 0.1 to 100%, especially from approximately 1 to approximately 50% or, in the case of lyophilisates, up to 100%, of the active ingredient.

Depending upon the type of infection and the condition of the infected organism, the daily dose used for the oral or parenteral treatment of a warm-blooded animal (human or animal) weighing approximately 70 kg is from approximately 100 mg to approximately 2 g.

The following Examples serve to illustrate the invention. Temperatures are given in degrees Centigrade.

The following abbreviations are used in the Examples:
TLC: thin-layer chromatograph
IR: infra-red spectrum
UV: ultraviolet spectrum
NMR: nuclear resonance spectrum
DBU: 1,5-diazabicyclo[5.4.0]undec-5-ene
THF: tetrahydrofuran
DMF: dimethylformamide
M.p.: melting point

EXPERIMENTAL SECTION

Example 1

(3S,4R)-3-(tert.-butyl-dimethyl-silyloxymethyl)-4-[5-(tetrazol-1-yl)-valeroylthio]-azetidin-2-one A mixture of 204.8 mg of 5-(tetrazol-1'-yl)-thiovaleric acid in 1.1 ml of sodium hydroxide solution and 5 ml of water is added at room temperature, while stirring, to a solution of 293 mg of 3-(tert.-butyldimethyl-silyloxymethyl)-4-methylsulphonylazetidin-2-one in 5 ml of absolute THF. The mixture is subsequently maintained at pH 10 by the addition of 0.1N sodium hydroxide solution. After a reaction time of two hours at room temperature, the mixture is diluted with ethyl acetate and the aqueous phase is separated off. Extraction is carried out twice with ethyl acetate and the combined extracts are washed with brine. After drying over sodium sulphate and concentration under a high vacuum, the residue is chromatographed over silica gel using toluene and ethyl acetate (1:2) as eluant.

TLC (silica gel): toluene/ethyl acetate (2:3) $R_f = 0.17$
IR (methylene chloride): 2.94, 5.66, 5.96 μm.

The starting compound, 5-(tetrazol-1'-yl)-thiovaleric acid, can be manufactured as follows:

(1aa) 5-(N-formylamino)-valeric acid ethyl ester 1.4 ml of triethylamine are added to 1.8 g of 5-aminovaleric acid ethyl ester hydrochloride in 40 ml of formic acid ethyl ester and the whole is then heated under reflux for 2 hours. The precipitate is filtered off, washed with a small quantity of formic acid ethyl ester and concentrated by evaporation under reduced pressure in a rotary evaporator. The residue is partitioned between methylene chloride and sodium bicarbonate solution, and the organic phase is then washed with brine, dried and concentrated by evaporation. The title compound is obtained in the form of an oil.

IR (methylene chloride): 5.78, 5.92, 6.64 μm.

(1ab) 5-isocyanovaleric acid ethyl ester 17.15 ml of triethylamine are added to 8.5 g of 5-(N-formylamino)-valeric acid ethyl ester in 50 ml of methylene chloride. While cooling with an ice bath, 25 ml of 20% phosgene solution in toluene are added dropwise thereto and the mixture is stirred at 0° for 1.5 hours. The reaction mixture is poured onto ice water and the organic phase is separated off, dried and concentrated by evaporation. The resulting title compound is purified by distillation.

B.p. (0.3 torr): 70°.
IR (methylene chloride): 4.68, 5.83, 7.3, 8.6 μm.

(1ac) 5-(tetrazol-1-yl)-valeric acid ethyl ester 3.6 g of 5-isocyanovaleric acid ethyl ester are heated at reflux temperature under argon for 24 hours in 72 ml of a 0.9M $HN_3$ solution in benzene. After concentration by evaporation and purification by chromatography on silica gel (eluant: toluene/ethyl acetate 1:1) the pure title compound is obtained.

IR (methylene chloride): 3.2, 5.85, 7.32 μm.

(1ad) 5-(tetrazol-1-yl)-valeric acid 2.12 g of (5-tetrazol-1-yl)-valeric acid ethyl ester are dissolved in 5 ml of methanol, and 4.28 ml of a methanolic NaOH solution (3N) are added. After stirring for 2.5 hours at room temperature, the solvent is distilled off and the residue is taken up in water. After washing with ethyl acetate, the aqueous phase is acidified (pH 3) and extracted twice with ethyl acetate. After drying and concentration by evaporation, the pure title compound is obtained.

NMR (DMSO.d$_6$): δ 12.1 ppm (1H, broad), 9.5 ppm (1H, s), 4.55 ppm (2H, t), 2.3 ppm (2H, t), 1.7 ppm (4H, m).

(1ae) 5-(tetrazol-1-yl)-valeric acid chloride 1 g of 5-(tetrazol-1-yl)-valeric acid in 12 ml of absolute benzene is heated at reflux temperature for 20 minutes with 0.6 ml of thionyl chloride and 2 drops of DMF. After concentration by evaporation under reduced pressure, the title compound is obtained.

IR (methylene chloride): 3.18, 5.62, 6.78 μm.

(1af) 5-(tetrazol-1-yl)-thiovaleric acid 5 g of 5-(tetrazol-1-yl)-valeric acid chloride are dissolved in 4.5 ml of absolute methylene chloride and, at 0°, this solution is added dropwise to 35.5 ml of a solution of pyridine and $H_2S$ in methylene chloride (30 ml of pyridine and 6 g of $H_2S$ in 100 ml of methylene chloride). The mixture is then stirred at 0° under a nitrogen atmosphere for 1 hour. The reaction mixture is taken up in chloroform, and the aqueous phase is acidified to pH 2 with 2N $H_2SO_4$ and extracted twice with chloroform. The combined organic phases are washed twice with 25 ml of 10% $NaHCO_3$ solution. The pH is then adjusted to 3 with 2N $H_2SO_4$ and the title compound is obtained by repeated extraction with chloroform. It is dried over sodium sulphate and concentrated.

IR (methylene chloride): 3.9, 5.9, 8.6, 9.1 μm.

The starting material, (3S,4R)-3-(tert.-butyl-dimethyl-silyloxymethyl)-4-methylsulphonylazetindin-2-one, can be manufactured as follows:

(1ba)
(3S,5R,6R)-2,2-dimethyl-6-(tert.-butyl-dimethylsilyloxymethyl)-penam-3-carboxylic acid methyl ester 1,1-dioxide A solution of 23.6 g (85 mmol) of (3S,5R,6R)-2,2-dimethyl-6-hydroxymethylpenam-3-carboxylic acid methyl ester in 50 ml of dimethylformamide is stirred at room temperature for 45 minutes with 25.5 g (170 mmol) of tert.-butyldimethylchlorosilane and 11.5 g (170 mmol) of imidazole. The solvent is then distilled off under a high vacuum and the residue is taken up in ethyl acetate. The solution is washed with 1N sulphuric acid and then with water, and the aqueous solutions are extracted twice with ethyl acetate. The organic phase is dried over sodium sulphate and concentrated in a rotary evaporator. The product is obtained in the form of a crystalline mass.

TLC silica gel, toluene/ethyl acetate (4:1): $R_f = 0.56$.
IR ($CH_2Cl_2$) 3.4, 5.57, 5.65 μm.

(1bb)
2-[(3S,4R)-3-(tert.-butyl-dimethyl-silyloxymethyl)-4-methylsulphonyl-2-oxoazetidin-1-yl]-3-methyl-2-butenoic acid methyl ester 9 ml of DBU are added to a solution of 202 g (0.51 mol) of (3R,5R,6R)-2,2-dimethyl-6-(tert.-butyl-dimethyl-silyloxymethyl)-penam-3-carboxylic acid methyl ester 1,1-dioxide in 800 ml of tetrahydrofuran and the whole is stirred at room temperature for 5 minutes. A further 95 ml of DBU are then added and the whole is stirred at room temperature for 30 minutes. Subsequently, 42.3 ml (0.68 mol) of methyl iodide are added while cooling. After a reaction period of 3 hours, the DBU-hydriodide that has crystallised is filtered off and the filtrate is concentrated. The residue is taken up in ethyl acetate and the solution is washed with 1N sulphuric acid, water and bicarbonate solution. The aqueous phases are extracted twice with ethyl acetate. The combined organic phases are dried over sodium sulphate and the solution is concentrated to a thick oil.

TLC silica gel, toluene/ethyl acetate (4:1): $R_f=0.42$.
IR (CH$_2$Cl$_2$): 5.63, 5.81, 6.17 μm.

(1bc)
(3S,4R)-3-hydroxymethyl-4-methylsulphonylazetidin-2-one and
(3S,4R)-3-(tert.-butyl-dimethyl-silyloxymethyl)-4-methylsulphonylazetidin-2-one A solution of 25 g (61.7 mmol) of 2-[(3S,4R)-3-(tert.-butyl-dimethyl-silyloxymethyl)-4-methylsulphonyl-2-oxoazetidin-1-yl]-3-methyl-2-butenoic acid methyl ester in 400 ml of methylene chloride is treated at −10° with an ozone/oxygen mixture. The disappearance of the starting material is monitored by thin layer chromatography. When the reaction is complete, 30 ml of dimethyl sulphide are added and the mixture is stirred for a further 3 hours at room temperature. The solution is concentrated and the residue is taken up in a mixture of 160 ml of methanol, 24 ml of ethyl acetate and 3 ml of water and heated for 40 minutes at 70° C. The solvent is then removed and the residue is evaporated twice in the presence of toluene. The crystallising oil is taken up in methylene chloride and the crystals, consisting of (3S,4R)-3-hydroxymethyl-4-methylsulphonylazetidin-2-one, are isolated by filtration. The filtrate is concentrated and (3S,4R)-3-(tert.-butyl-dimethyl-silyloxymethyl)-4-methylsulphonylazetidin-2-one is obtained in pure form by chromatography over silica gel with toluene/ethyl acetate (3:1):

(3S,4R)-3-hydroxymethyl-4-methylsulphonylazetidin-2-one:
TLC silica gel, toluene/ethyl acetate (1:1): $R_f=0.36$.
IR (CH$_2$Cl$_2$): 2.96, 3.54, 5.61 μm.

(3S,4R)-3-(tert.-butyl-dimethyl-silyloxymethyl)-4-methylsulphonylazetidin-2-one:
TLC silica gel, toluene/ethyl acetate (1:1): $R_f=0.06$.

24 g (183 mmol) of tert.-butyldimethylchlorosilane and 11 g (163 mmol) of imidazole are added in the course of 45 minutes at room temperature to a solution of 14.6 g (81.5 mmol) of (3S,4R)-3-hydroxymethyl-4-methylsulphonylazetidin-2-one in 40 ml of dimethylformamide. The solvent is then removed under a high vacuum and the residue is taken up in ethyl acetate. The organic phase is washed in succession with 1N sulphuric acid, water and sodium bicarbonate solution. The aqueous phases are extracted twice with ethyl acetate. The combined organic phases are dried over sodium sulphate and concentrated in a rotary evaporator. The crystalline residue is pure (3S,4R)-3-tert.-butyl-dimethyl-silyloxymethyl)-4-methylsulphonylazetidin-2-one.

EXAMPLE 2

2-[(3S,4R)-3-tert.-butyl-dimethyl-silyloxymethyl-4-[5-(tetrazol-1-yl)-valeroylthio]-2-oxoazetidin-1-yl]-2-hydroxyacetic acid 2-trimethylsilyl ethyl ester 2.4 g of molecular sieve (type 4 Å 1/16 by Messrs Dr. Bender & Dr. Hobein AG, Zurich) are added to a mixture of 248 mg of (3S,4R)-3-(tert.-butyl-dimethylsilyloxymethyl)-4-[5-(tetrazol-1-yl)-valeroylthio]-azetidin-2-one and 273.5 mg of glyoxylic acid 2-trimethylsilyl ethyl ester-hemiketal in 5.3 ml of toluene and 1.06 ml of DMF and the whole is stirred at a bath temperature of 100° under protective gas for 5 hours. After cooling, the mixture is filtered through Hyflo and the filtration residue is washed with toluene. Concentration of the filtrate by evaporation and drying at 40° under a high vacuum yields the product in the form of a yellow oil.

TLC (silica gel) toluene/ethyl acetate (2:3):
$R_f=0.31$ and 0.2.
IR (methylene chloride): 2.86, 5.67, 5.78, 5.96 μm.

EXAMPLE 3

2-[(3S,4R)-3-tert.-butyl-dimethyl-silyloxymethyl-4-[5-(tetrazol-1-yl)-valeroylthio]-2-oxoazetidin-1-yl]-2-triphenylphosphoranylideneacetic acid 2-trimethylsilyl ethyl ester While stirring at −15°, to a solution of 700 mg of 2-[(3S,4R)-3-tert.-butyl-dimethyl-silyloxymethyl-4-[5-(tetrazol-1-yl)-valeroylthio]-2-oxoazetidin-1-yl]-2-hydroxyacetic acid 2-trimethylsilyl ethyl ester in 4.3 ml of tetrahydrofuran there are added, in succession, over a period of 10 minutes 0.13 ml of thionyl chloride and 0.25 ml of triethylamine. The white suspension is stirred at 0° for 1 hour and filtered through Hyflo. After washing with toluene, the residue is concentrated in a rotary evaporator and dried under a high vacuum. The residue is dissolved in 3.7 ml of dioxan, and 0.28 g of triphenylphosphine and 0.12 ml of 2,6-lutidine are added and the whole is stirred at 50° for 18 hours. The mixture is filtered through Hyflo and this residue is washed with toluene. The combined filtrates are concentrated by evaporation, and chromatography of the residue over 40 g of silica gel with toluene/ethyl acetate (4:1) yields the pure product.

TLC (silica gel) toluene/ethyl acetate (2:3): $R_f=0.28$.
IR (methylene chloride): 5.72, 5.93, 6.23, 9.1 μm.

EXAMPLE 4

(5R,6S)-2-[4-(tetrazol-1-yl)-butyl]-6-tert.-butyldimethyl-silyloxymethyl)-2-penem-3-carboxylic acid 2-trimethylsilyl ethyl ester 0.8 g of 2-[(3S,4R)-3-tert.-butyl-dimethylsilyloxymethyl-4-[5-(tetrazol-1-yl)-valeroylthio]-2-oxoazetidin-1-yl]-2-triphenylphosphoranylideneacetic acid 2-trimethylsilyl ethyl ester are dissolved in 300 ml of toluene and the whole is stirred at reflux temperature under a nitrogen atmosphere for 1.25 hours. Concentration of the solvent by evaporation and chromatography of the residue on silica gel with the eluant toluene/ethyl acetate (2:1) yields the pure product.

TLC (silica gel) toluene/ethyl acetate (2:3): $R_f=0.45$.
IR (methylene chloride): 5.62, 5.92, 6.34, 7.65 μm.

EXAMPLE 5

(5R,6S)-2-[4-(tetrazol-1-yl)-butyl]-6-hydroxymethyl-2-penem-3-carboxylic acid 2-trimethylsilyl ethyl ester 163 mg of (5R,6S)-2-[4-(tetrazol-1-yl)-butyl]-6-tert.-butyl-dimethyl-silyloxymethyl-2-penem-3-carboxylic acid 2-trimethylsilyl ethyl ester are dissolved in 4.8 ml of absolute THF and, after cooling to −80°, under a nitrogen atmosphere 0.17 ml of acetic acid are added. 18.2 ml of a 0.1M tetrabutylammonium fluoride solution in THF are then added dropwise and the mixture is allowed to rise to room temperature and is then stirred at this temperature for 2 hours. The volume of solvent is concentrated to 2 ml in a rotary evaporator and the residue is partitioned between 25.3 mg of sodium bicarbonate in 10 ml of water and 10 ml of ethyl acetate. The organic phase is separated off and the aqueous phase is extracted twice more with ethyl acetate. The organic extracts are washed once more with water and dried over sodium sulphate. Concentration by evaporation under a high vacuum yields the crude product which is chromatographed over 10 g of silica gel with the eluant toluene/ethyl acetate (1:1).

TLC (silica gel) toluene/ethyl acetate (2:3): $R_f = 0.12$.

IR (methylene chloride): 2.78, 5.62, 5.92, 6.33, 7.65 μm.

EXAMPLE 6

Sodium (5R,6S)-2-[4-(tetrazol-1-yl)-butyl]-6-hydroxymethyl-2-penem-3-carboxylate 106 mg of (5R,6S)-2-[4-(tetrazol-1-yl)-butyl]-6-hydroxymethyl-2-penem-3-carboxylic acid 2-trimethylsilyl ethyl ester are dissolved in 2 ml of absolute THF and the whole is cooled to −30°. After the addition of 10 ml of tetrabutylammonium fluoride solution in THF, the temperature is increased to 0°. After stirring for 10 minutes at this temperature, 13 ml of ethyl acetate and 13 ml of water are added to the mixture. The solution is then adjusted to pH 3 by the dropwise addition of 4N HCl in an ice bath. The aqueous phase is then separated off and the ethyl acetate phase is extracted with 10.6 ml of a 0.05M NaCHO₃ solution. The organic phase is extracted once more with 0.5 ml of NaCHO₃ (0.05M) and 4 ml of H₂O. The combined aqueous phases are freed of the remaining solvent in vacuo and lyophilised.

UV (water) $\lambda_{max} = 305$ nm.

EXAMPLE 7

2-[(3S,4R)-3-(tert.-butyl-dimethyl-silyloxymethyl)-4-[2-(tetrazol-1-yl)-acetylthio]-2-oxoazetidin-1-yl]-2-triphenylphosphoranylideneacetic acid allyl ester 5 g of the silver salt of 2-[(3S,4R)-3-(tert.-butyl-dimethyl-silyloxymethyl)-4-mercapto-2-oxo-azetidin-1-yl]-2-triphenylphosphoranylideneacetic acid allyl ester are dissolved in 50 ml of absolute methylene chloride, and first of all 0.99 ml of pyridine is added and then the whole is treated dropwise at 0° with a solution of 2-(tetrazol-1-yl)acetic acid chloride over a period of 10 minutes. After stirring for one hour at 0°, the cooling bath is removed and stirring is continued for 15 minutes at room temperature. After the insoluble material has been filtered off through Hyflo, the filtrate is washed with aqueous sodium bicarbonate solution and then with brine, dried and concentrated by evaporation. The pure compound is obtained by chromatogaphy over silica gel (eluant: toluene/ethyl acetate from 6:1 to 1:1)

IR (methylene chloride): 5.71, 5.92, 6.18 μm.

The starting material, 2-[(3S,4R)-3-(tert.-butyl-dimethyl-silyloxymethyl)-4-mercapto-2-oxo-azetidin-1-yl]-2-triphenylphosphoranylideneacetic acid allyl ester (silver salt), is obtained as follows:

(7aa)
(3S,4R)-3-(tert.-butyl-dimethyl-silyloxymethyl)-4-triphenylmethylthioazetidin-2-one 12.5 g of triphenylmethylmercaptan are suspended in 70 ml of methanol at 0°, and a total of 2.2 g of a 50% sodium hydride suspension in oil is added thereto in portions over a period of 10 minutes. Subsequently, an emulsion of 11.1 g of 3-(tert.-butyl-dimethyl-silyloxymethyl)-4-methylsulphonylazetidin-2-one in 70 ml of acetone and 70 ml of water are added dropwise over a period of 30 minutes. After stirring for 30 minutes at 0° and for 1 hour at room temperature, the reaction mixture is concentrated in a rotary evaporator, methylene chloride is added and the aqueous phase is separated off. The organic solution is washed with brine and dried over sodium sulphate. After concentration, the crude title compound is purified by chromatography on silica gel (eluant: toluene/ethyl acetate 19:1).

TLC (toluene/ethyl acetate 19:1): $R_f = 0.64$.

IR (methylene chloride): 2.95, 5.68, 8.95, 12.0 μm.

(7ab)
2-[(3S,4R)-3-(tert.-butyl-dimethyl-silyloxymethyl)-4-triphenylmethylthio-2-oxoazetidin-1-yl]-2-hydroxyacetic acid allyl ester 27 g of molecular sieve (4 Å) are added to 8.4 g of (3S,4R)-3-(tert.-butyl-dimethyl-silyloxymethyl)-4-triphenylmethylthioazetidin-2-one and 8.23 g of glyoxylic acid allyl ester-hemiacetal in 170 ml of absolute toluene and the whole is stirred for 10 hours at 55°. After filtration and concentration in a rotary evaporator under reduced pressure, the crude product is purified by chromatography over silica gel (eluant: toluene/ethyl acetate 95:5).

TLC (silica gel, toluene/ethyl acetate 10:1): $R_f = 0.37$ and 0.27.

IR (CH₂Cl₂) 2.84, 5.68, 5.73 μm.

(7ac)
2-[(3S,4R)-3-(tert.-butyl-dimethyl-silyloxymethyl)-4-triphenylmethylthio-2-oxoazetidin-1-yl]-2-triphenylphosphoranylideneacetic acid allyl ester While stirring at −15°, to a solution of 604 mg of 2-[(3S,4R)-3-(tert.-butyl-dimethyl-silyloxymethyl)-4-triphenylmethylthio-2-oxoazetidin-1-yl]-2-hydroxyacetic acid allyl ester in 5 ml of tetrahydrofuran there are added, in succession, over a period of 5 minutes 80 μl of thionyl chloride and 88 μl of pyridine. The white suspension is then stirred for 1 hour at −10° and filtered through Hyflo. After washing the residue with toluene, concentration is effected in a rotary evaporator. The residue is dissolved in 3 ml of dioxan; 293 mg of triphenylphosphine and 0.13 ml of 2,6-lutidine are added and the whole is stirred at a bath temperature of 115° for 2 hours. The mixture is filtered through Hyflo and the residue is then washed with toluene. The combined filtrates are concentrated by evaporation. Chromatography of the residue over silica gel yields the pure product (eluant: toluene/ethyl acetate 95:5)

TLC (silica gel, toluene/ethyl acetate 1:1): $R_f = 0.18$.

IR (CH₂Cl₂): 5.73, 6.23 μm.

(7ad) Silver salt of
2-[(3S,4R)-3-(tert.-butyl-dimethyl-silyloxymethyl)-4-mercapto-2-oxo-azetidin-1-yl]-2-tri-phenylphosphoranylideneacetic acid allyl ester 7.5 g of 2-[(3S,4R)-3-(tert.-butyl-dimethylsilyloxymethyl)-4-triphenylmethylthio-2-oxoazetidin-1-yl]-2-triphenylphosphoranylideneacetic acid allyl ester are placed in 87 ml of ether, and at room temperature 70 ml of a 0.5M aqueous silver nitrate solution are added. A mixture of 3.6 ml of tributylamine, 0.18 ml of trifluoroacetic acid and 25 ml of ether is then added dropwise thereto and the reaction mixture is stirred for 20 minutes. The solid material is filtered with suction and washed with ether, water and again with ether. Finally for purification, the solid material is again made into a slurry in 40 ml of ether and 40 ml of water, filtered with suction and dried.

IR (CH$_2$Cl$_2$): 5.68, 6.17 μm.

A solution of the starting material, 2-(tetrazol-1-yl)-acetic acid chloride, can be manufactured as follows:

(7ba) 2-(tetrazol-1-yl)-acetic acid ethyl ester 23.7 ml of isocyanoacetic acid ethyl ester are added dropwise to 500 ml of a 1.3N hydrazoic acid (HN$_3$) solution in benzene and the reaction mixture is then heated under reflux for 24 hours. After concentration, the crude title compound is purified by chromatography over silica gel (eluant: toluene/ethyl acetate 1:1).

IR (methylene chloride): 3.16, 5.73, 6.80, 8.23 μm.

(7bb) 2-(tetrazol-1-yl)-acetic acid

In a manner analogous to that described in Example (1ad), 25.6 g of 2-(tetrazol-1-yl)-acetic acid ethyl ester are reacted to form the title compound.

IR (tetrahydrofuran): 5.73 μm.

(7bc) 2-(tetrazol-1-yl)-acetic acid chloride 1.58 g of 2-(tetrazol-1-yl)-acetic acid are suspended in 27 ml of absolute methylene chloride, and 1.9 ml of 1-chloro-1-dimethylaminoisobutene (CDIB) are added. After stirring for 30 minutes at room temperature, a further 0.5 ml of CDIB is added and stirring is continued for a further 90 minutes. This solution of the acid chloride [IR (methylene chloride): 3.20, 5.57 μm] is further reacted directly.

EXAMPLE 8

2-[(3S,4R)-3-(tert.-butyl-dimethyl-silyloxymethyl)-4-[3-(tetrazol-1-yl)-propionylthio]-2-oxoazetidin-1-yl]-2-triphenylphosphoranylideneacetic acid allyl ester In a manner analogous to that described in Example 7, 5 g of the silver salt of Example (7ad) are reacted with a solution of 3-(tetrazol-1-yl)-propionic acid chloride to form the title compound.

IR (methylene chloride): 5.88, 5.92, 6.17 μm.

The starting material, 3-(tetrazol-1-yl)-propionic acid chloride, is manufactured as follows:

(8a) 3-(tetrazol-1-yl)-propionic acid 4.5 g of tetrazole are stirred for 8 hours at 90° with 4.5 ml of acrylic acid and 15 drops of pyridine. After cooling, 150 ml of water are added to the reaction mixture and the whole is acidified with HCl (concentrated) and concentrated under reduced pressure in a rotary evaporator. The crystalline residue is digested three times with methyl ethyl ketone and the combined organic phases are dried over sodium sulphate. After concentration by evaporation, the crystalline residue is stirred with isopropanol/ether and filtered off.

NMR (DMSO-d$_6$): δ=3.0 (2H, t); 4.7 (2H, t); 9.5 (1H, s) and 8–11 ppm (1H, broad).

(8b) 3-(tetrazol-1-yl)-propionic acid chloride

In a manner analogous to that described in Example (7bc), 1.75 g of 3-(tetrazol-1-yl)-propionic acid are reacted to form the title compound.

The resulting solution is further reacted immediately.

IR (methylene chloride): 3.18, 5.63 μm.

EXAMPLE 9

2-[(3S,4R)-3-(tert.-butyl-dimethyl-silyloxymethyl)-4-[4-(tetrazol-1-yl)-butyroylthio]-2-oxoazetidin-1-yl]-2-triphenylphosphoranylideneacetic acid allyl ester In a manner analogous to that described in Example 7, 5 g of the silver salt obtained in Example (7ad) are dissolved in 10 ml of absolute methylene chloride, 1.13 ml of pyridine are added and, after cooling to 0°, the whole is reacted with 2.61 g of 4-(tetrazol-1-yl)-butyric acid chloride to form the title compound.

IR (methylene chloride): 5.71, 5.93, 6.17 μm.

The starting material, 4-(tetrazol-1-yl)-butyric acid chloride, is manufactured as follows:

(9a) 4-(tetrazol-1-yl)-butyric acid ethyl ester 4 ml of orthoformic acid triethyl ester and 6 ml of acetic acid are added to 0.84 g of 4-aminobutyric acid ethyl ester hydrochloride and 0.9 g of sodium azide and the whole is heated under reflux for 7 hours. After cooling, the reaction mixture is taken up in ethyl acetate and aqueous sodium bicarbonate solution, the organic phases are separated off and washed four times with aqueous sodium bicarbonate solution. After washing with water and brine, the ethyl acetate phase is dried over sodium sulphate and concentrated to form the title compound.

IR (methylene chloride): 3.16, 5.81, 6.76, 8.4 μm.

(9b) 4-(tetrazol-1-yl)-butyric acid 6.65 g of 4-(tetrazol-1-yl)-butyric acid ethyl ester are stirred in 42.7 ml of acetic acid, 8.1 ml of concentrated HCl and 17.2 ml of water for 3 hours at 100°. After cooling, the reaction mixture is concentrated three times each with toluene and ether under reduced pressure in a rotary evaporator. After drying under a high vacuum, the title compound is obtained.

NMR (DMSO-d$_6$): δ=2.3 (4H, m); 4.6 (2H, t); 8.7 (1H, broad) and 9.53 ppm (1H, s).

(9c) 4-(tetrazol-1-yl)-butyric acid chloride

In a manner analogous to Example (1ae), 0.31 g of 4-(tetrazol-1-yl)-butyric acid are converted into the title compound.

IR (methylene chloride): 3.18, 5.62 μm.

EXAMPLE 10

2-[(3S,4R)-3-(tert.-butyl-dimethyl-silyloxymethyl)-4-[3-(1,2,4-triazol-1-yl)-propionylthio]-2-oxoazetidin-1-yl]-2-triphenylphosphoranylideneacetic acid allyl ester In a manner analogous to that described in Example 7, a solution of 3-(1,2,4-triazol-1-yl)-propionic acid chloride is reacted with 5 g of the silver salt described under Example (7ad) to form the title compound.

IR (methylene chloride): 5.72, 5.92, 6.17 μm.

The starting material, 3-(1,2,4-triazol-1-yl)-propionic acid chloride, is manufactured as follows:

(10a) 3-(1,2,4-triazol-1-yl)-propionic acid

In a manner analogous to that described in Example (8a), 2.8 g of 1,2,4-triazole are reacted with 2.88 g of acrylic acid to form the title compound.

IR (KBr): 3.21, 5.85, 6.58 μm.

(10b) 3-(1,2,4-triazol-1-yl)-propionic acid chloride

In a manner analogous to that described in Example (7bc), 1.72 g of 3-(1,2,4-triazol-1-yl)-propionic acid are reacted to form the title compound.

IR (methylene chloride): 5.62 μm.

EXAMPLE 11

(5R,6S)-2-[(tetrazol-1-yl)-methyl]-6-(tert.-butyl-dimethyl-silyloxymethyl)-2-penem-3-carboxylic acid allyl ester In a manner analogous to that described in Example 4, 2.3 g of 2-[(3S,4R)-3-(tert.-butyl-dimethyl-silyloxymethyl)-4-[2-(triazol-1-yl)-acetylthio]-2-oxo- azetidin-1-yl]-2-triphenylphosphoranylideneacetic acid allyl ester are reacted after heating for 25 minutes to form the title compound.

IR (methylene chloride): 5.60, 5.90, 6.33 μm.

EXAMPLE 12

(5R,6S)-2-[2-(tetrazol-1-yl)-ethyl]-6-(tert.-butyl-dimethyl-silyloxymethyl)-2-penem-3-carboxylic acid allyl ester In a manner analogous to that described in Example 4, 4 g of 2-[(3S,4R)-3-(tert.-butyl-dimethyl-silyloxymethyl)-4-[3-(tetrazol-1-yl)-propionylthio]-2-oxo-azetidin-1-yl]-2-triphenylphosphoranylideneacetic acid allyl ester are converted after heating for 45 minutes into the title compound.

IR (methylene chloride): 5.62, 5.90, 6.33 μm.

EXAMPLE 13

(5R,6S)-2-[3-(tetrazol-1-yl)-propyl]-6-(tert.-butyl-dimethyl-silyloxymethyl)-2-penem-3-carboxylic acid allyl ester In a manner analogous to that described in Example 4, 3.2 g of 2-[(3S,4R )-3-(tert.-butyl-dimethyl-silyloxymethyl)-4-[4-(tetrazol-1-yl)-butyroylthio]-2-oxoazetidin-1-yl]-2-triphenylphosphoranylideneacetic acid allyl ester are converted after heating for 2 hours into the title compound.

IR (methylene chloride): 5.62, 5.88, 6.33 μm.

EXAMPLE 14

(5R,6S)-2-[2-(1,2,4-triazol-1-yl)-ethyl]-6-(tert.-butyl-dimethyl-silyloxymethyl)-2-penem-3-carboxylic acid allyl ester In a manner analogous to that described in Example 4, 3.2 g of 2-[(3S,4R )-3-(tert.-butyl-dimethylsilyloxymethyl)-4-[3-(1,2,4-triazol-1-yl)-propionylthio]-2-oxoazetidin-1-yl]-2-triphenylphosphoranylideneacetic acid allyl ester are converted after heating for 75 minutes into the title compound.

IR (methylene chloride): 5.61, 5.88, 6.33 μm.

EXAMPLE 15

(5R,6S)-2-[(tetrazol-1-yl)-methyl]-6-hydroxymethyl-b 2-penem-3-carboxylic acid allyl ester In a manner analogous to that described in Example 5, 1.15 g of (5R,6S)-2-[(tetrazol-1-yl)-methyl]-6-(tert.-butyl-dimethyl-silyloxymethyl)-2-penem-3-carboxylic acid allyl ester are reacted to form the title compound.

IR (KBr): 5.64, 5.86, 6.33 μm.

EXAMPLE 16

(5R,6S)-2-[(tetrazol-1-yl)-ethyl]-6-hydroxymethyl-2-penem-3-carboxylic acid allyl ester In a manner analogous to that described in Example 5, 1.65 g of (5R,6S)-2-[2-(tetrazol-1-yl)-ethyl]-6-(tert.-butyl-dimethyl-silyloxymethyl)-2-penem-3-carboxylic acid allyl ester are converted into the title compound.

IR (methylene chloride): 2.78, 5.62, 5.88, 6.33 μm.

EXAMPLE 17

(5R,6S)-2-[3-(tetrazol-1-yl)-propyl]-6-hydroxymethyl-2-penem-3-carboxylic acid allyl ester In a manner analogous to that described in Example 5, 1.2 g of (5R,6S)-2-[3-(tetrazol-1-yl)-propyl]-6-(tert.-butyl-dimethyl-silyloxymethyl)-2-penem-3-carboxylic acid allyl ester are converted into the title compound.

IR (methylene chloride): 2.77, 5.62, 5.88, 6.33 μm.

EXAMPLE 18

(5R,6S)-2-[2-(1,2,4-triazol-1-yl)-ethyl]-6-hydroxymethyl-2-penem-3-carboxylic acid allyl ester In a manner analogous to that described in Example 5, 2.85 g of (5R,6S)-2-[2-(1,2,4-triazol-1-yl)-ethyl]-6-(tert.-butyl-dimethyl-silyloxymethyl)-2-penem-3-carboxylic acid allyl ester are converted into the title compound.

IR (methylene chloride): 2.78, 5.62, 5.30, 6.35 μm.

EXAMPLE 19

Sodium salt of (5R,6S)-2-[(tetrazol-1-yl)-methyl]-6-hydroxymethyl-2-penem-3-carboxylic acid 22 mg of tetrakis(triphenylphosphine)palladium and, subsequently, 0.31 ml of tributyltin hydride are added at −10° to a solution of 310 mg of (5R,6S-2-[(tetrazol-1-yl)-methyl]-6-hydroxymethyl-2-penem-3-carboxylic acid allyl ester in 12 ml of absolute THF. After stirring for 25 minutes at −10°, 0.065 ml of acetic acid is added and the reaction mixture is stirred at the same temperature for 10 minutes. After concentration in a rotary evaporator, the residue is taken up in water/ethyl acetate, the aqueous phase is adjusted to pH 8.5 with sodium bicarbonate and separated off. After again washing with ethyl acetate, the title compound is purified by chromatography over XAD/2 (eluant: water). The appropriate fractions are lyophilised under a high vacuum.

UV (phosphate buffer pH 7.4): $\lambda_{max}=308$ nm.

EXAMPLE 20

(5R,6S)-2-[2-(tetrazol-1-yl)-ethyl]-6-hydroxymethyl-2-penem-3-carboxylic acid

In a manner analogous to that described in Example 19, 725 mg of (5R,6S)-2-[2-(tetrazol-1-yl)-ethyl]-6-hydroxymethyl-2-penem-3-carboxylic acid allyl ester are converted into the title compound.

UV (phosphate buffer pH 7.4): $\lambda_{max}=304$ nm.

EXAMPLE 21

Sodium salt of (5R,6S)-2-[3-(tetrazol-1-yl)-propyl]-6-hydroxymethyl-2-penem-3-carboxylic acid In a manner analogous to that described in Example 19, 0.74 g of (5R,6S)-2-[3-(tetrazol-1-yl)-propyl]-6- hydroxymethyl-2-penem-3-carboxylic acid allyl ester are converted into the title compound.

UV (water): $\lambda_{max}=302$ nm.

EXAMPLE 22

Sodium salt of (5R,6S)-2-[2-(1,2,4-triazol-1-yl)-ethyl]-6-hydroxymethyl-2-penem-3-carboxylic acid In a manner analogous to that described in Example 19, 0.64 g of (5R,6S)-2-[2-(1,2,4-triazol-1-yl)-6-hydroxymethyl-2-penem-3-carboxylic acid allyl ester are converted into the title compound.

UV (phosphate buffer pH 7.4): $\lambda_{max}=303$ nm.

EXAMPLE 23: (3R,S)-3-(tetrazol-1-yl)-butyric acid (a) (3R,S)-(tetrazol-1-yl)-butyric acid methyl ester 10 g of tetrazole are dissolved in 50 ml of crotonic acid methyl ester and 10 drops of pyridine are added. The reaction mixture is then stirred for 18 hours at 90°. After cooling, the mixture is 3 times taken up in toluene and concentrated in a rotary evaporator. The crude product is purified by column chromatography (toluene/ethyl acetate 1:1), TLC (silica gel, toluene/ethyl acetate 1:1): $R_f=0.26$.

(b) (3R,S)-3-(tetrazol-1-yl)-butyric acid 53.2 ml of acetic acid, 10.6 ml of concentrated hydrochloric acid and 21.3 ml of water are added to 9.05 g of (3R,S)-3-(tetrazol-1-yl)-butyric acid methyl ester and the whole is heated under reflux for 3 hours. After cooling, the mixture is concentrated to dryness. The residue is concentrated three times with toluene under a water-jet vacuum and then digested twice with ether. After filtration, the solid portion is dried under a high vacuum.

NMR (DMSO d$_6$): $\delta=9.55$ (s, 1H), 7.9 (broad), 5.2 (m, 1H), 3.0 (d, 2H), 1.6 ppm (d, 3H).

EXAMPLE 24: (3R,S)-3-(tetrazol-1-yl)-butyric acid chloride 1.5 ml of thionyl chloride and 6 drops of absolute DMF are added to 2.34 g of (3R,S)-3-(tetrazol-1-yl)-butyric acid in 30 ml of absolute toluene and the whole is stirred for 1 hour at 80°. After cooling, the reaction mixture is concentrated in a rotary evaporator, concentrated by evaporation a further three times in the presence of methylene chloride and dried under a high vacuum.

IR (CH$_2$Cl$_2$): 1780 cm$^-$.

EXAMPLE 25: (3R,S)-3-(pyrrol-1-yl)-butyric acid chloride 2.47 g of (3R,S)-3-(pyrrol-1-yl)-butyric acid [Chem. Pharm. Bull. 30, 2586 (1982)] are dissolved in 30 ml of absolute methylene chloride and 2.64 ml of 1-dimethylamino-1-chloro-2-methylpropene are added. The reaction mixture is stirred for 2 hours 15 minutes at room temperature and further reacted as described in Example 11 without being isolated.

EXAMPLE 26:

2-[(3S,4R)-3-(tert.-butyl-dimethylsilyloxymethyl)-4-[(3R,S)-3-(tetrazol-1-yl)-butyroylthio]-2-oxoazetidin-1-yl]-2-triphenylphosphoranylideneacetic acid allyl ester 5 g of the silver salt of 2-[(3S,4R)-3-(tert.-butyl-dimethylsilyloxymethyl)-4-mercapto-2-oxoazetidin-1-yl]-2-triphenylphosphoranylideneacetic acid 2-allyl ester are dissolved in 100 ml of absolute methylene chloride, cooled to 0° and 85 mg of 4-dimethylaminopyridine and 1.23 ml of pyridine are added. After 1.9 g of 3-(tetrazol-1-yl)-butyric acid chloride have been added, the reaction mixture is stirred for 30 minutes at 0°. The precipitate is filtered off, the filtrate is diluted with methylene chloride and washed with aqueous NaCHO$_3$ solution and then with brine. After drying over Na$_2$SO$_4$, the solution is concentrated and the residue is chromatographed over silica gel (eluant toluene/ethyl acetate).

TLC (silica gel, toluene/ethyl acetate 1:1): $R_f=0.18$;
IR (CH$_2$Cl$_2$): 1750, 1680, 1610 cm$^{-1}$.

EXAMPLE 27:

(5R,6S)-2-[(2R,S)-2-(tetrazol-1-yl)-prop-1-yl]-6-(tert.-butyl-dimethylsilyloxymethyl)-2-penem-3-carboxylic acid allyl ester A solution of 3.4 g of 2-[(3S,4R)-3-tert.-butyl-dimethylsilyloxymethyl)-4-[(3R,S)-3-(terazol-1yl-butyroyl-thio]-2-oxoazetidin-1-yl]-2-triphenylphosphoranylideneacetic acid allyl ester in 500 ml of toluene is stirred for 2 hours under an argon atmosphere at reflux temperature. The solvent is then concentrated by evaporation and the crude product is purified by chromatography over silica gel (eluant toluene/ethyl acetate 9:1).

TLC (silica gel, ethyl acetate); $R_f=0.55$;
IR (CH$_2$Cl$_2$): 1780, 1695; 1575 cm$^{-1}$.

EXAMPLE 28: (5R,6S)-2-[(2R,S)-2-(tetrazol-1-yl)-prop-1-yl]-6-hydroxymethyl-2-penem-3-carboxylic acid allyl ester A solution of 1.5 g of (5R,6S)-2-[(2R,S)-2-(tetrazol-1-yl)-prop-1-yl]-6-(tert.-butyl-dimethylsilyloxymethyl)-2-penem-3-carboxylic acid allyl ester in 32 ml of absolute THF is cooled to $-70°$ and there are added in succession 1.31 ml of acetic acid and, dropwise over a period of 15 minutes, 70 ml of a 0.1M tetrabutylammonium fluoride solution in THF. The cooling bath is then removed and the reaction mixture is slowly brought to room temperature. After stirring for 5 hours at room temperature, the reaction mixture is concentrated in a rotary evaporator and taken up in ethyl acetate and aqueous NaCHO$_3$. The organic phase is separated off, washed with brine, dried over Na$_2$SO$_4$ and concentrated. The crude product is purified by chromatography over silica gel (eluant toluene/ethyl acetate 4:1 to 1:1).

TLC (silica gel, ethyl acetate): $R_f=0.22$;
IR (CH$_2$Cl$_2$): 3600, 1780, 1695, 1575 cm$^{-1}$.

EXAMPLE 29: Sodium salt of (5R,6S)-2-[(2R,S)-2-(tetrazol-1-yl)-prop-1-yl]-6-hydroxymethyl-2-penem-3-carboxylic acid 0.85 g of (5R,6S)-2-[(2R,S)-(tetrazol-1-yl)-prop-1-yl]-6-hydroxymethyl-2-penem-3-carboxylic acid allyl ester is dissolved in 32 ml of absolute THF and cooled to $-10°$ and 53 mg of tetrakis-triphenylphosphine palladium and 0.75 ml of tributyltin hydride are added. After stirring for 35 minutes at $-10°$, 0.16 ml of acetic acid are added and the reaction mixture is stirred for a further 10 minutes at $-5°$. After concentration in a rotary evaporator, the residue is taken up in water/ethyl acetate, cooled and adjusted to pH 7.5 with NaCHO$_3$. The aqueous phase is separated off, washed twice with ethyl acetate, concentrated in a rotary evaporator and purified on an XAD-2 column (eluant:water). The combined fractions are lyophilised under a high vacuum.

TLC (reversed phase Opti UPC 12, water): $R_f=0.3$;
UV (phosphate buffer pH 7.4): $\lambda$max.$=304$ nm.

EXAMPLE 30:
2-[(3S,4R)-3-(tert.-butyl-dimethylsilyl-oxymethyl)-4-[(3R,S)-3-(pyrrol-1-yl)]-butyroylthio]-2-oxoazetidin-1-yl]-2-triphenylphosphoranylideneacetic acid allyl ester Analogously to Example 26,5 g of the silver salt of 2-[3S,4R)-3-(tert.-butyl-dimethylsilyloxymethyl)-4-mercapto-2-oxoazetidin-1-yl]-2-triphenylphosphoranylideneacetic acid 2-allyl ester and 1.5 molar equivalents of 3-(pyrrol-1-yl)-butyric acid chloride are reacted to form the title compound.

TLC (silica gel, ethyl acetate) $R_f=0.62$;
IR (CH$_2$Cl$_2$): 1750, 1680, 1625 cm$^{-1}$.

EXAMPLE 31:
(5R,6S)-2-[(2R,S)-2-(pyrrol-1-yl)-prop-1-yl]-6-(tert.-butyl-dimethylsilyloxymethyl)-2-penem-3-carboxylic acid allyl ester Analogously to Example 27, 3.86 g of 2-[(3S,4R)-3-(tert.-butyl-dimethylsilyloxymethyl)-4-[(3R,S)-3-(pyrrol-1-yl)-butyroylthio]-2-oxoazetidin-1-yl]-2-triphenylphosphoranylideneacetic acid allyl ester are converted into the title compound.

TLC (silica gel, toluene/ethyl acetate 1:1): $R_f=0.7$;
IR (CH$_2$Cl$_2$): 1780, 1700, 1575 cm$^{-1}$.

EXAMPLE 32:
(5R,6S)-2-[(2R,S)-2-(pyrrol-1-yl)-prop-1-yl]-6-hydroxymethyl-2-penem-3carboxylic acid allyl ester Analogously to Example 28, 1.5 g of (5R,6S)-2-[(2R,S)-2-(pyrrol-1-yl)-prop-1-yl]-6-(tert.-butyl-dimethylsilyloxymethyl)-2-penem-3-carboxylic acid allyl ester are converted into the title compound.

TLC (silica gel; toluene/ethyl acetate 1:1): $R_f=0.35$;
IR (CH$_2$Cl$_2$): 3600, 1780, 1695, 1575 cm$^{-1}$.

EXAMPLE 33: Sodium salt of (5R,6S)-2-[(2R,S)-2-(pyrrol-1-yl)-prop-1-yl]-6-hydroxymethyl-2-penem-3-carboxylic acid Analogously to Example 29, 1 g of (5R,6S)-2-[(2R,S)-2-(pyrrol-1-yl)-prop-1-yl]-6-hydroxymethyl-2-penem-3-carboxylic acid allyl ester is converted into the title compound.

TLC (reversed phase; Opti UPC 12, water/acetonitrile 4:1): $R_f=0.38$;
UV (water): $\lambda$max.$=308$ nm.

EXAMPLE 34: (3R,S)-3-(tetrazol-1-yl)-thiobutyric acid 2 g of (3R,S)-3-(tetrazol-1-yl)-butyric acid chloride in 4 ml of absolute methylene chloride are added at 0° to an excess of a pyridine/hydrogen sulphide solution in methylene chloride. The reaction mixture is stirred for 1 hour at 0°, diluted with chloroform and rendered acidic using 2N sulphuric acid. The aqueous solution is extracted a further twice with chloroform. The combined organic phases are extracted with aqueous NaCHO$_3$ solution. After acidification of the extracts with H$_2$SO$_4$ (2N) and washing several times with chloroform, the organic solution is dried over Na$_2$SO$_4$ and concentrated to dryness by evaporation. The title compound is obtained.

IR (CH$_2$Cl$_2$): 2560, 1695 cm$^{-1}$.

EXAMPLE 35:
(3S,4R)-3-(tert.-butyl-dimethylsilyloxymethyl)-4-[(3R,S)-3-tetrazol-1-yl)-butyroylthio]-azetidin-2-one 8.2 g of (3S,4R)-3-(tert.-butyl-dimethylsilyloxymethyl)-4-methylsulphonylazetidin-2-one and 6.7 g of (3R,S)-3-(tetrazol-1-yl)-thiobutyric acid are dissolved in 180 ml of methylene chloride; 180 ml of water and 42 ml of 1N NaOH are added. The emulsion is stirred vigorously for 1.5 hours at room temperature. The organic phase is separated off and the aqueous phase is extracted a further twice with CH$_2$Cl$_2$. The combined organic extracts are washed with a saturated aqueous NaCHO$_3$ solution and then with brine, dried over Na$_2$SO$_4$ and concentrated by evaporation. The resulting crude product is purified by chromatography over silica gel.

IR (CH$_2$Cl$_2$): 3425, 1765, 1685 cm$^{-1}$.

The manufacture of the starting material (3S,4R)-3-(tert.-butyl-dimethylsilyloxymethyl)-4-methylsulphonylazetidin-2-one is described in Example 1.

EXAMPLE 36:
2-[(3S,4R)-3-(tert.-butyl-dimethylsilyloxymethyl)-4-[(3R,S)-3-(tetrazol-1-yl)-butyroylthio]-2-oxoazetidin-1-yl]-2-hydroxyacetic acid allyl ester Analogously to Example (7ab), 8.1 g of (3S,4R)-3-(tert.-butyl-dimethylsilyloxymethyl)-4-[(3R,S)-3-(tetrazol-1-yl)-butyroylthio]-azetidin-2-one are reacted to form the title compound.

IR (CH$_2$Cl$_2$): 3515, 1760, 1745, 1685 cm$^{-1}$.

EXAMPLE 37:
2-[(3S,4R)-3-(tert.-butyl-dimethylsilyloxymethyl)-4-[(3R,S)-3-(tetrazol-1-yl)-butyroylthio]-2-oxoazetidin-1-yl]-2-triphenylphosphoranylideneacetic acid allyl ester Analogously to Example (7ac), 7.43 g of 2-[(3S,4R)-3-(tert.-butyl-dimethylsilyloxymethyl)-4-[(3R,S)-3-(tetrazol-1-yl)-butyroylthio]-2-oxoazetidin-1-yl]-2-hydroxyacetic acid allyl ester are reacted to form the title compound.

TLC (silica gel, toluene/ethyl acetate 1:1): $R_f=0.18$;
IR (CH$_2$Cl$_2$): 1750, 1680, 1610 cm$^{-1}$.

The product is identical with that of Example 26.

EXAMPLE 38

2-[(3S,4R)-3-(tert.-butyl-dimethyl-silyloxymethyl)-4-[2-(tetrazol-1-yl)-acetylthio]-2-oxoazetidin-1-yl]-2-triphenylphosphoranylideneacetic acid allyl ester (see Example 7) can also be manufactured as follows:

(38a)
2-[(3S,4R)-3-(tert.-butyl-dimethyl-silyloxymethyl)-4-chloroacetylthio-2-oxoazetidin-1-yl]-2-triphenylphosphoranylideneacetic acid allyl ester In a manner analogous to that described in Example 7, 30 g of the silver salt of 2-[(3S,4R)-3-(tert.-butyl-dimethyl-silyloxymethyl)-4-mercapto-2-oxoazetidin-1-yl]-2-triphenylphosphoranylideneacetic acid allyl ester are reacted with 5.04 ml of chloroacetyl chloride to form the title compound.

IR (methylene chloride): 5.71, 5.95, 6.19 $\mu$m.

(38b)
2-[(3S,4R)-3-(tert.-butyl-dimethyl-silyloxymethyl)-4-[2-(tetrazol-1-yl)-acetylthio]-2-oxo-azetidin-1-yl]-2-triphenylphosphoranylideneacetic acid allyl ester 0.68 g of 2-[(3S,4R)-3-(tert.-butyl-dimethylsilyloxymethyl)-4-chloroacetylthio-2-oxoazetidin-1-yl]-2-triphenylphosphoranylideneacetic acid allyl ester are dissolved in 5 ml of DMF, and 91 mg of tetrazole-sodium are added. After stirring for 16 hours, the reaction mixture is taken up in water/ethyl acetate. The organic phase is separated off, dried and concentrated. The product is purified by chromatography over silica gel (eluant: toluene/ethyl acetate 1:1).

IR (methylene chloride): 5.71, 5.92, 6.18 μm.

EXAMPLE 39

(5R,6S)-2-[(tetrazol-1-yl)-methyl]-6-(tert.-butyl-dimethyl-silyloxymethyl)-2-penem-3-carboxylic acid allyl ester (see Example 11) can also be manufactured as follows:

(39a)
(5R,6S)-2-chloromethyl-6-(tert.-butyl-dimethylsilyloxymethyl)-2-penem-3-carboxylic acid allyl ester In a manner analogous to that described in Example 4, 0.341 g of 2-[(3S,4R)-3-(tert.-butyl-dimethylsilyloxymethyl)-4-chloroacetylthio-2-oxoazetidin-1-yl]-2-triphenylphosphoranylideneacetic acid allyl ester (see Example (38a)) are converted after heating for 45 minutes into the title compound.

IR (methylene chloride): 5.60, 5.86, 6.33 μm.

(39b)
(5R,6S)-2-[tetrazol-1-ylmethyl]-6-(tert.-butyl-dimethyl-silyloxymethyl)-2-penem-3-carboxylic acid allyl ester 0.4 g of (5R,6S)-2-chloromethyl-6-(tert.-butyl-dimethyl-silyloxymethyl)-2-penem-3-carboxylic acid allyl ester are dissolved in 5 ml of DMF, and 91 mg of tetrazole-sodium are added. After stirring for 16 hours, the reaction mixture is taken up in water/ethyl acetate. The organic phase is separated off, dried and concentrated. The product is purified by chromatography over silica gel (eluant: toluene/ethyl acetate 9:1).

IR (methylene chloride): 5.60, 5.90, 6.33 μm.

EXAMPLE 40

(5R,6S)-2-[2-(tetrazol-1-yl)-ethyl]-6-hydroxymethyl-2-penem-3-carboxylic acid 1-ethoxycarbonyloxyethyl ester 1.2 g of sodium iodide are dissolved in 3.7 ml of acetone, and 0.275 ml of ethyl-1-chloroethyl carbonate are added. The mixture is stirred at room temperature for 3 hours. The solution is then added dropwise to 15.0 ml of methylene chloride and the inorganic salts that are formed are filtered off. The methylene chloride solution is concentrated to 2 ml and, at 0°, is added to a solution of 0.3 g of (5R,6S)-2-[2-(tetrazol-1-yl)-ethyl]-6-hydroxymethyl-2-penem-3-carboxylic acid in 4 ml of dimethylacetamide. The mixture is then stirred for 3 hours at 0°, diluted with ethyl acetate and washed three times with water. The organic phases are dried over sodium sulphate and concentrated in a rotary evaporator. The crude product is purified over 10 g of silica gel using ethyl acetate as eluant. The title compound is obtained in the form of a white foam.

IR spectrum (methylene chloride): absorption bands at 5.59, 5.75 μm.

EXAMPLE 41

(5R,6S)-2-[2-(tetrazol-1-yl)-ethyl]-6-hydroxymethyl-2-penem-3-carboxylic acid pivaloyloxymethyl ester 0.6 g of sodium iodide are dissolved in 2 ml of acetone, and 0.15 ml of pivalic acid chloromethyl ester are added. The mixture is stirred at room temperature for 3 hours and then added dropwise to 7.5 ml of methylene chloride. The inorganic salts that are formed are filtered off. The methylene chloride solution is concentrated to 1 ml and, at 0°, added to a solution of 0.1 g of (5R,6S)-2-[2-(tetrazol-1-yl)-ethyl]-6-hydroxymethyl-2-penem-3carboxylic acid and 0.07 ml of diisopropylethylamine in 4 ml of N,N-dimethylacetamide.

Stirring is then carried out at 0° for 3 hours, and the whole is then diluted with ethyl acetate and washed three times with water. The organic phase is dried over sodium sulphate and concentrated in a rotary evaporator. The crude product is purified over 10 g of silica gel using ethyl acetate as eluant. The title compound is obtained in the form of a white foam.

IR spectrum (methylene chloride): absorption bands at 5.59 and 5.78 μm.

EXAMPLE 42

In an analogous manner to that described in the preceding Examples, the following compounds are obtained:

sodium salt of (5R,6S)-2-[(2R,S)-2-(tetrazol-1-yl)-but-1-yl]-6-hydroxymethyl-2-penem-3-carboxylic acid, UV (water): λmax=306 nm;

sodium salt of (5R,6S)-2-[(2R,S)-2-(1,2,4-triazol-1-yl)-prop-1-yl]-6-hydroxymethyl-2-penem-3-carboxylic acid, UV (phosphate buffer pH 7.4) λmax=303 nm;

(5R,6S)-2-[(2R,S)-2-(5-aminotetrazol-1-yl)-prop-1-yl]-6-hydroxymethyl-2-penem-3-carboxylic acid, UV (water): λmax=305 nm;

sodium salt of (5R,6S)-2-[(2R,S)-2-(imidazol-1-yl)-prop-1-yl]-6-hydroxymethyl-2-penem-3-carboxylic acid, UV (water): λmax=308 nm;

sodium salt of (5R,6S)-2-[(2R,S)-2-(pyrazol-1-yl)-prop-1-yl]-6-hydroxymethyl-2-penem-3-carboxylic acid, UV (water): λmax=309 nm;

sodium salt of (5R,6S)-2-[(1R,S)-1-(tetrazol-1-yl)ethyl]-6-hydroxymethyl-2-penem-3-carboxylic acid, UV (phosphate buffer pH 7.4): λmax=305 nm;

sodium salt of (5R,6S)-2-[(2R,S)-2-(tetrazol-1-yl)-prop-1-yl]-6-[(1R)-hydroxyethyl]-2penem-3-carboxylic acid, UV (water): λmax=306 nm;

sodium salt of (5R,6S)-2-[(2R,S)-2-(tetrazol-1-yl)-prop-1-yl]-6-(2-hydroxyprop-2-yl)-2-penem-3-carboxylic acid, UV (water): λmax=307 nm;

(5R,6S,8R)-2-[(tetrazol-1-yl)-methyl]-6-(1-hydroxyethyl)-2-penem-3-carboxylic acid, sodium salt, UV (phosphate buffer pH 7.4): $\lambda_{max}$=307 nm;

(5R.,6S,8R)-2-[2-(tetrazol-1-yl)-ethyl]-6-(1-hydroxyethyl)-2-penem-3-carboxylic acid, sodium salt, UV (phosphate buffer pH 7.4): $\lambda_{max}$=308 nm;

(5R,6S)-2-[(2R,S)-2-(tetrazol-1-yl)-prop-1-yl]-6-hydroxymethyl-2-penem-3-carboxylic acid 1-ethoxycarbonyloxyethyl ester, IR spectrum (methylene chloride): absorption bands at 1788 and 1740 cm⁻¹.

(5R,6S)-2-[(2R,S)-2-(pyrrol-1-yl)-prop-1-yl]-6-hydroxymethyl-2-penem-3-carboxylic acid 1-ethoxycarbonyloxyethyl ester, IR spectrum (methylene chloride): 1786 and 1743 cm⁻¹;

(5R,6S)-2-[(2R,S)-2-(tetrazol-1-yl)-prop-1-yl]-6-hydroxymethyl-2-penem-3-carboxylic acid pivaloyloxymethyl ester, IR spectrum (methylene chloride): absorption bands at 1790 and 1730 cm⁻¹;

(5R,6S)-2-[(2R,S)-2-(pyrrol-1-yl)-prop-1-yl]-6-hydroxymethyl-2-penem-3-carboxylic acid pivaloyloxymethyl ester, IR spectrum (methylene chloride): 1789 and 1726 cm⁻¹.

EXAMPLE 43:(5R,6S)-2-[4-(tetrazol-1-yl)-but-1-yl]-6-[(1R)-1-allyloxycarbonyloxyethyl]-2-penem-3-carboxylic acid allyl ester A solution of 2.5 g of 2-[(3S,4R)-3-[(1R)-1-allyloxycarbonyloxyethyl]-4-[5-(tetrazol-1-yl)-pentanoylthio]-2-oxo-azetidin-1-yl]-2-triphenylphosphoranylideneacetic acid allyl ester in 500 ml of toluene is stirred under an argon atmosphere for 3.5 hours at reflux temperature. The solvent is then evaporated off and the crude product is purified by chromatography over silica gel. (Eluant toluene/ethyl acetate 85:15), $R_f$ (ethyl acetate)=0.55; IR (CH$_2$Cl$_2$): 1790, 1745, 1705, 1585, 1315, 1240 cm$^{-1}$.

The starting material can be manufactured as follows:

(a) 5-(tetrazol-1-yl)-valeric acid ethyl ester 13 g of sodium azide and 59 ml of triethyl orthoformate are added to a solution of 13.4 g of 5-amino-valeric acid ethyl ester hydrochloride in 89 ml of acetic acid and the whole is stirred for 6 hours at 100°. The reaction mixture is cooled and partitioned betwen ethyl acetate and water. The organic phase is washed several times with saturated sodium bicarbonate solution and once with brine and, after drying over sodium sulphate, is concentrated. After purification by chromatography over silica gel (eluant: toluene/ethyl acetate 4:1 to 7:3), the pure title compound is obtained. $R_f$ (toluene/ethyl acetate 1:1); 0.32.

IR (CH$_2$Cl$_2$): 2950, 1725 cm$^{-1}$.

(b) 5-(tetrazol-1-yl)-valeric acid 2.12 g of 5-(tetrazol-1-yl)-valeric acid ethyl ester are dissolved in 5 ml of methanol, and 4.28 ml of a methanolic NaOH solution (3N) are added thereto. After stirring for 2.5 hours at room temperature, the solvent is distilled off and the residue is taken up in water. After washing with ethyl acetate, the aqueous phase is acidified (pH 3) and extracted twice with ethyl acetate. After drying and concentrating by evaporation, the pure title compound is obtained.

NMR (60 MHz, DMSO.d$_6$): $\delta$12.1 (1H, broad), 9.5 (1H, s), 4.55 (2H, t), 2.3 (2H, t), 1.7 ppm (4H, m).

(c) 5-(tetrazol-1-yl)-valeric acid chloride 1 g of 5-(tetrazol-1-yl)-valeric acid is heated for 20 minutes at reflux temperature in 12 ml of absolute benzene with 0.6 ml of thionyl chloride and 2 drops of DMF. After concentration by evaporation under reduced pressure, the title compound is obtained.

IR (methylene chloride): 3145, 1780, 1475 cm$^{-1}$.

(d) 2-[(3S,4R)-3-[(1R)-1-allyloxycarbonyloxyethyl]-4-[5-(tetrazol-1-yl)-pentanoylthio]-2-oxo-azetidin-1-yl]-2-triphenylphosphoranylideneacetic acid allyl ester 1.74 g of the silver salt of 2-[(3S,4R)-3-[(1R)-1-allyloxycarbonyloxyethyl]-4-mercapto-2-oxo-azetidin-1-yl]-2-triphenylphosphoranylideneacetic acid allyl ester are dissolved in 30 ml of methylene chloride, and, at 0°, 0.41 ml of pyridine, 50 mg of 4-dimethylaminopyridine and then, dropwise, a solution of 0.87 g of 5-(tetrazol-1-yl)-valeric acid chloride in 15 ml of methylene chloride are added. After stirring for 30 minutes at 0°, the solid material is filtered off over Hyflo and the filtrate is washed with aqueous sodium bicarbonate solution and then with brine. After drying over MgSO$_4$, the solution is concentrated by evaporation. The residue is purified by chromatography over silica gel (eluant toluene/ethyl acetate: 9:1 to 1:1). TLC (ethyl acetate) $R_f$=0.33; IR (CH$_2$Cl$_2$): 1750, 1690, 1620 cm$^{-1}$.

EXAMPLE 44:The sodium salt of (5R,6S)-2-[4-(tetrazol-1-yl)-but-1-yl]-6-[(1R)-1-hydroxyethyl]-2-penem-3-carboxylic acid 95 mg of tetrakis-triphenylphosphine-palladium and 1.13 ml of tributyltin hydride are added to a solution of 0.9 g of (5R,6S)-2-[4-(tetrazol-1-yl)-but-1-yl]-6-[(1R)-1-allyloxycarbonyloxyethyl]-2-penem-3-carboxylic acid allyl ester in 34 ml of absolute THF. After stirring for 30 minutes at room temperature, 0.58 ml of acetic acid is added to the mixture dropwise and the whole is stirred for a further 15 minutes. After concentration in a rotary evaporator, the mixture is taken up in water/ethyl acetate, rendered neutral by means of NaHCO$_3$ and washed twice with ethyl acetate. The agueous phase is concentrated in a rotary evaporator and the title substance is purified by subsequent chromatography on reversed-phase Opti UPC 12 with water. The combined fractions are lyophilised under a high vacuum.

TLC (reversed-phase Opti UPC 12, water): $R_f$=0.5. UV (water): $\lambda_{max}$=303 nm.

EXAMPLE 45:(5R,6S)-2-[7-(tetrazol-1-yl)-hept-1-yl]-6-[(1R)-1-allyloxycarbonyloxyethyl]-2-penem-3-carboxylic acid allyl ester A solution of 2.5 g of 2-[(3S,4R)-3-[(1R)-1-allyloxycarbonyloxyethyl]-4-8 (tetrazol-1-yl)-octanoylthio]-2-oxo-azetidin-1-yl]-2-triphenylphosphoranylideneacetic acid allyl ester in 500 ml of toluene is stirred under an argon atmosphere for 3.5 hours at reflux temperature. The solvent is then evaporated off and the crude product is purified by chromatography over silica gel. (Eluant toluene/ethyl acetate 85:15), IR (CH$_2$Cl$_2$): 2940, 1790, 1745, 1710, 1580 cm$^{-1}$.

The starting material can be manufactured as follows:

(a) 8-(tetrazol-1-yl)-octanoic acid ethyl ester

Analogously to Example (43a), 19 g of 8-amino-octanoic acid hydrochloride are converted into the title compound.

IR (CH$_2$Cl$_2$): 2940, 1725, 1168 cm$^{-1}$.

(b) 8-(tetrazol-1-yl)-octanoic acid

Analogously to Example (43b),11.3 g of 8-(tetrazol-1-yl)-octanoic acid ethyl ester are converted into the title compound.

$^1$H-NMR (60 MHz, DMSO.d$_6$): $\delta$=1.3–2.0 (m, 10 H); 2.25 (t, 2H); 4.5 (t, 2H); 9.5 (s, 1H); 8.5–10 ppm (br, 1H).

(c) 2-[(3S,4R)-3-[(1R)-1-allyloxycarbonyloxyethyl]-4-[8-(tetrazol-1-yl)-octanoylthio]-2-oxo-azetidin-1-yl]-2-triphenylphosphoranylideneacetic acid allyl ester Analogously to Example (43), 2.12 g of 8-(tetrazol-1-yl)-octanoic acid are converted into the title compound.

IR (CH$_2$Cl$_2$): 1755, 1700, 1630 cm$^{-1}$.

EXAMPLE 46:The sodium salt of (5R,6S)-2-[7-(tetrazol-1-yl)-hept-1-yl]-6-[(1R)-1-hydroxyethyl]-2-penem-3-carboxylic acid 80 mg of tetrakis-triphenylphosphine-palladium and 0.95 ml of tributyltin hydride are added to a solution of 735 mg of (5R,6S)-2-[7-(tetrazol-1-yl)-hept-1-yl]-6-

[(1R)-1-allyloxycarbonyloxyethyl]-2-penem-3-carboxylic acid allyl ester in 30 ml of absolute THF. After stirring for 30 minutes at room temperature, 0.49 ml of acetic acid is added to the mixture dropwise and the whole is stirred for a further 15 minutes. After concentration in a rotary evaporator, the mixture is taken up in water/ethyl acetate, rendered neutral by means of $NaHCO_3$ and washed twice with ethyl acetate. The aqueous phase is concentrated in a rotary evaporator and the title substance is purified by subsequent chromatography on reversed-phase Opti UPC 12 with water. The combined fractions are lyophilised under a high vacuum.

UV (water): $\lambda_{max}=302$ nm.

EXAMPLE 47:(5R,6S)-2-[5-(tetrazol-1-yl)-pent-1-yl]-6-[(1R)-1-allyloxycarbonyloxyethyl]-2-penem-3-carboxylic acid allyl ester Analogously to Example 43, 1.7 g of 2-[(3S,4R)-3-[(1R)-1-allyloxycarbonyloxyethyl]-4-[6-(tetrazol-1-yl)-hexanoylthio]-2-oxo-azetidin-1-yl]-2-triphenylphosphoranylideneacetic acid allyl ester are converted into the title compound.

IR ($CH_2Cl_2$): 2940, 1790, 1742, 1705, 1580 $cm^{-1}$.

The starting material can be manufactured as follows:

(a) 6-(tetrazol-1-yl)-hexanoic acid ethyl ester

Analogously to Example (43a), 14 g of 6-aminohexanoic acid hydrochloride are converted into the title compound.

IR ($CH_2Cl_{12}$): 2940, 1725, 1170 $cm^{-1}$.

(b) 6-(tetrazol-1-yl)-hexanoic acid

Analogously to Example (43b), 8.1 g of 6-(tetra-zol-1-yl)-hexanoic acid ethyl ester are converted into the title compound.

$^1$H-NMR (60 MHz, DMSO-$d_6$): $\delta=1.4$ (m, 4H); 1.8 (m, 2H); 2.2 (t, 2H); 4.5 (t, 2H); 9.5 (s, 1H); 12 ppm (br, 1H).

(c) 2-[(3S,4R)-3-[(1R)-1-allyloxycarbonyloxyethyl]-4-[6-(tetrazol-1-yl)-hexanoylthio]-2-oxo-azetidin-1-yl]-2-triphenylphosphoranylideneacetic acid allyl ester 1.52 ml of 1-dimethylamino-1-chloro-2-methylpropene are added at room temperature to a suspension of 1.84 g of 6-(tetrazol-1-yl)-hexanoic acid in 40 ml of absolute methylene chloride and the whole is stirred for 2 hours at room temperature. This reaction mixture is then added dropwise, at 0°, to a solution of 3.48 g of the silver salt of 2-[(3S,4R)-3-[(1R)-1allyloxycarbonyloxyethyl]-4-mercapto-2-oxo-azetidin-1-yl]-2-triphenylphosphoranylideneacetic acid allyl ester, 0.82 ml of pyridine and 0.1 g of 4-dimethylaminopyridine in 55 ml of absolute methylene chloride. After 30 minutes, the solid material is filtered off and the filtrate is washed with an aqueous sodium bicarbonate solution and then with brine. After drying over magnesium sulphate, concentration is carried out and the residue is purified by chromatography over silica gel (eluant toluene/ethyl acetate 9:1 to 1:1). TLC (ethyl acetate) $R_f=0.28$, IR ($CH_2Cl_2$): 1755, 1695, 1620 $cm^{-1}$.

EXAMPLE 48: The sodium salt of (5R,6S)-2-[5-(tetrazol-1-yl)-pent-1-yl]-6-[(1R)-1-hydroxyethyl]-2-penem-3-carboxylic acid Analogously to Example 44,0.58 g of (5R,6S)-2-[5-(tetrazol-1-yl)-pent-1-yl]-6-[(1R)-1-allyloxycarbonyloxyethyl]- 2-penem-3-carboxylic acid allyl ester is converted into the title compound.

UV (water): $\lambda_{max}=302$ nm.

EXAMPLE 49: (5R,6S)-2-[10-(tetrazol-1-yl)-dec-1-yl]-6-[(1R)-1-allyloxycarbonyloxyethyl]-2-penem-3-carboxylic acid allyl ester Analogously to Example 43, 2.6 g of 2-[(3S,4R)-3-[(1R)-1-allyloxycarbonyloxyethyl]-4-[11-(tetrazol-1-yl)-undecanoylthio]-2-oxo-azetidin-1-yl]-2-triphenylphosphoranylideneacetic acid allyl ester are converted into the title compound.

IR ($CH_2Cl_2$): 2930, 1790, 1745, 1705, 1635, 1580 $cm^{-1}$.

The starting material can be manufactured as follows:

(a) 11-(tetrazol-1-yl)-undecanoic acid ethyl ester

Analogously to Example (43a),10.5 g of 11-aminoundecanoic acid hydrochloride are converted into the title compound.

IR ($CH_2Cl2$): 2930, 1725, 1165 $cm^{-1}$.

(b) 11-(tetrazol-1-yl)-undecanoic acid

Analogously to Example (43b),6.5 g of 11-(tetrazol-1-yl)-undecanoic acid ethyl ester are converted into the title compound.

$^1$H-NMR (60 MHz, DMSO.$d_6$): $\delta=1.3–2.1$ (m, 16H); 2.25 (t, 2H); 4.5 (t, 2H); 9.5 ppm (s, 1H).

(c) 2-[(3S,4R)-3-[(1R)-1-allyloxycarbonyloxyethyl]-4-11-(tetrazol-1-yl)-undecanoylthio]-2-oxo-azetidin-1yl]-2-triphenylphosphoranylideneacetic acid allyl ester Analogously to Example (47c),3.48 g of 11-(tetrazol-1-yl)-undecanoic acid are converted into the title compound.

IR ($CH_2Cl_2$): 2930, 1750, 1635 $cm^{-1}$.

EXAMPLE 50: The sodium salt of (5R,6S)-2-[10-(tetrazol-1-yl)-dec-1-yl]-dec-1-yl]-6-[(1R)-1-hydroxyethyl]-2-penem-3-carboxylic acid Analogously to Example 44, 0.72 g of (5R,6S)-2-[10-(tetrazol-1-yl)-dec-1-yl]-6-[(1R)-1-allyloxycarbonyloxyethyl]-2-penem-3-carboxylic acid allyl ester is converted into the title compound.

UV (water): $\lambda_{max}=302$ nm.

EXAMPLE 51: (5R,6S)-2-[3-(tetrazol-1-yl)-prop-1-yl]-6-[(1R)-1-allyloxycarbonyloxyethyl]-2-penem-3-carboxylic acid allyl ester Analogously to Example 43, 3.4 g of 2-[(3S,4R)-3-[(1R)-1-allyloxycarbonyloxyethyl]-4-[4-tetrazol-1-yl)-butanoylthio]-2-oxo-azetidin-1-yl]-2-triphenylphosphoranylideneacetic acid allyl ester are converted into the title compound.

IR ($CH_2Cl_2$): 1790, 1745, 1705, 1580 $cm^{-1}$.

The starting material can be manufactured as follows:

2-[(3S,4R)-3-[(1R)-1-allyloxycarbonyloxyethyl]-4-[4-(tetrazol-1-yl)-butanoylthio]-2-oxo-azetidin-1-yl]-2-triphenylphosphoranylideneacetic acid allyl ester Analogously to Example (47c),2 g of 4-(tetrazol-1-yl)-butyric acid are converted into the title compound.

IR ($CH_2Cl_2$): 1760; 1690; 1620 $cm^{-1}$.

EXAMPLE 52: The sodium salt of (5R,6S)-2-[3-(tetrazol-1-yl)-prop-1-yl]-6-[(1R)-1-hydroxyethyl]-2-penem-3-carboxylic acid Analogously to Example 44, 0.56 g of (5R,6S)-2-[3-(tetrazol-1-yl)-prop-1-yl]-6-[(1R)-1-allyloxycarbonyloxyethyl]-2-penem-3-carboxylic acid allyl ester is converted into the title compound.

UV (water): $\lambda_{max}=303$ nm.

EXAMPLE 53: (5R,6S)-2-[3-(tetrazol-1-yl)-prop-1-yl]-6-[(1R)-1-hydroxyethyl]-2-penem-3-carboxylic acid acetoxymethyl ester A solution of 70 mg of the sodium salt of (5R,6S)-2-[3-(tetrazol-1-yl)-prop-1-yl]-6-[(1R)-1-hydroxyethyl]-2-penem-3-carboxylic acid in 1.5 ml of absolute DMF is cooled to 0° and 40 mg of acetoxymethyl bromide are added thereto. After 35 minutes, a further 20 mg of acetoxymethyl bromide are added and the reaction mixture is then stirred for one hour at room temperature. The mixture is partitioned between water and ethyl acetate and the organic phase is then washed twice with brine. After drying over sodium sulphate, the whole is concentrated by evaporation under reduced pressure and the title compound is purified by chromatography over silica gel (eluant toluene up to toluene/ethyl acetate: 3:1). TLC (ethyl acetate) $R_f=0.23$.

IR ($CH_2Cl_2$): 3590, 1790, 1762, 1720, 1575 cm$^{-1}$.
UV (ethanol): $\lambda_{max}=322$ nm.

EXAMPLE 54: (5R,6S)-2-[3-(tetrazol-1-yl)-prop-1-yl]-[(1R)-1-hydroxyethyl]-2-penem-3-carboxylic acid pivaloyloxymethyl ester A solution of 70 mg of the sodium salt of (5R,6S)-2-[3-(tetrazol-1-yl)-prop-1-yl]-6-[(1R)-1-hydroxyethyl]-2-penem-3-carboxylic acid in 1.5 ml of absolute DMF is cooled to 0°, 53 μl of pivaloyloxymethyl iodide are added thereto and the whole is stirred for 70 minutes at that temperature. The reaction mixture is diluted with ethyl acetate, washed three times with brine, dried over sodium sulphate and concentrated. After drying under a high vacuum, the title compound is purified by chromatography over silica gel (eluant: toluene up to toluene/ethyl acetate: 3:1). TLC (ethyl acetate) $R_f=0.28$.

IR ($CH_2Cl_2$): 3600, 1790, 1748, 1722, 1580 cm$^{-1}$.
UV (EtOH): $\lambda_{max}=323$ nm.

EXAMPLE 55: (5R,6S)-2-[3-(tetrazol-1-yl)-prop-1-yl]-6-[(1R)-1-hydroxyethyl]-2-penem-3-carboxylic acid 1-ethoxycarbonyloxyethyl ester 1.2 g of sodium iodide are dissolved in 3.7 ml of acetone, and 0.275 ml of ethyl-1-chloroethyl carbonate is added thereto. The mixture is stirred for 3 hours at room temperature. The solution is then added dropwise to 15 ml of methylene chloride and the inorganic salts which precipitate are filtered off. The methylene chloride solution is concentrated to 2 ml and, at 0°, added to a solution of 0.347 g (1 mmol) of (5R,6S)-2-[3-(tetrazol-1-yl)-prop-1-yl]-6-[(1R)-1-hydroxyethyl]-2-penem-3-carboxylic acid in 4 ml of dimethylacetamide. The whole is stirred for 3 hours at 0° and then diluted with ethyl acetate and washed 3 times with water. The organic phases are dried over sodium sulphate and concentrated in a rotary evaporator. The crude product is purified over 10 g of silica gel using the eluant ethyl acetate. The title compound is obtained in the form of a white foam. IR spectrum (methylene chloride): 3590; 1790; 1748; 1720; 1665 cm$^{-1}$.

EXAMPLE 56

Dry-filled ampoules or phials containing 0.5 g of the sodium salt of (5R,6S)-2-[(2R,S)-2-(tetrazol-1-yl)-prop-1-yl]-6-hydroxymethyl-2-penem-3-carboxylic acid as active ingredient are manufactured as follows:

Composition (for 1 ampoule or phial)
active ingredient: 0.5 g
mannitol: 0.05 g

A sterile aqueous solution of the active ingredient and the mannitol is subjected to freeze-drying under aseptic conditions in 5 ml ampoules or 5 ml phials and the ampoules or phials are sealed and tested.

Instead of the above-mentioned active ingredient, it is also possible to use the same quantity of a different active ingredient of the preceding Examples, such as, for example, of the sodium salt of (5R,6S)-2-[3-(tetrazol-1-yl)-prop-1-yl]-6-[(1R)-1-hydroxyethyl]-2-penem-3-carboxylic acid or of the sodium salt of (5R,6S)-2-[7-(tetrazol-1-yl)-hept-1-yl]-6-[(1R)-1-hydroxyethyl]-2-penem-3-carboxylic acid.

I claim:

1. A penem compound of the formula

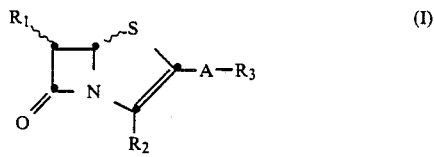

(I)

having the (5R,6S) configuration in which
$R_1$ represents methyl or ethyl, each substituted by hydroxy;
$R_2$ represents carboxy or esterified carboxy that can be cleaved under physiological conditions;
$R_3$ represents a tetrazolyl radical that is bonded via a tertiary ring nitrogen atom; and
A represents straight-chained lower alkylen substituted by lower alkyl,
or a pharmaceutically acceptable salt thereof.

2. The compound of claim 1 wherein
$R_1$ represents hydroxymethyl or 1-hydroxyethyl;
$R_2$ represents carboxy, 1-lower alkoxycarbonyloxy-lower alkoxycarbonyl or lower alkanoyloxymethoxycarbonyl;
$R_3$ represents 1H-tetrazol-1-yl or 2H-tetrazol-2-yl; and
A represents straight-chained lower alkylene having from 1 to 4 carbon atoms that is mono- or di-substituted by lower alkyl having 1 or 2 carbon atoms;
or a pharmaceutically acceptable salt thereof.

3. The compound of claim 1 wherein
$R_1$ represents hydroxymethyl or 1-hydroxyethyl;
$R_2$ represents carboxy;
$R_3$ represents 1H-tetrazol-1-yl; and
A represents 1,2-propylene;
or a pharmaceutically acceptable salt thereof.

4. (5R,6S)-2-[(2R,S)-2-(tetrazol-1-yl)-prop-1-yl]-6-hydroxymethyl-2-penem-3-carboxylic acid or a pharmaceutically acceptable salt thereof according to claim 1.

5. A penem compound of the formula

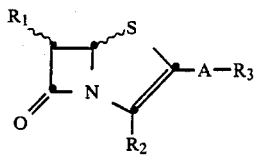

having the (5R,6S) configuration in which
$R_1$ represents methyl or ethyl, each substituted by hydroxy;
$R_2$ represents carboxy or esterified carboxy that can be cleaved under physiological conditions;
$R_3$ represents a tetrazolyl radical that is bonded via a tertiary ring nitrogen atom; and
A represents straight-chained lower alkylene having from 1 to 4 carbon atoms,
or a pharmaceutically acceptable salt thereof.

6. The compound of claim 5 wherein
$R_1$ represents hydroxymethyl or 1-hydroxyethyl;
$R_2$ represents carboxy, 1-lower alkoxycarbonyloxy-lower alkoxycarbonyl or lower alkanoyloxymethoxycarbonyl;
$R_3$ represents 1H-tetrazol-1-yl or 2H-tetrazol-2-yl; and
A represents straight-chained lower alkylene having from 1 to 4 carbon atoms;
or a pharmaceutically acceptable salt thereof.

7. The compound of claim 5 wherein
$R_1$ represents hydroxymethyl;
$R_2$ represents carboxy;
$R_3$ represents 1H-tetrazol-1-yl; and
A represents straight-chained lower alkylene having from 1 to 4 carbon atoms;
or a pharmaceutically acceptable salt thereof.

8. (5R,6S)-2-[4-1H-tetrazol-1-yl)-bytyl]-hydroxymethyl-2-penem-3-carboxylic acid or a pharmaceutically acceptable salt thereof according to claim 5.

9. (5R,6S)-2-[(tetrazol-1-yl)-methyl]-6-hydroxymethyl-2-penem-3-carboxylic acid or a pharmaceutically acceptable salt thereof according to claim 5.

10. (5R,6S)-2-[2-tetrazol-1-yl)-ethyl]-6-hydroxymethyl-2-penem-3-carboxylic acid or a pharmaceutically acceptable salt thereof according to claim 5.

11. (5R,6S)-2-[3-(tetrazol-1-yl)-propyl]-6-hydroxymethyl-2-penem-3-carboxylic acid or a pharmaceutically acceptable salt thereof according to claim 5.

12. A compound of the formula

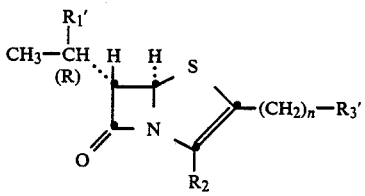

wherein
$R_1'$ represents hydroxy;
$R_2$ represents carboxy or an esterified carboxy group that can be cleaved under physiological conditions,
$R_3'$ represents a tetrazolyl radical that is bonded via a ring nitrogen atom; and
n represents an integer from 3 to 12;

or a pharmaceutically acceptable salt thereof.

13. The compound of claim 12 wherein
$R_1'$ represents hydroxy;
$R_2$ represents carboxy or esterified carboxy that can be cleaved under physiological conditions;
$R_3'$ represents 1-tetrazolyl or 2-tetrazolyl; and
n represents an integer from 3 to 10;
or a pharmaceutically acceptable salt thereof.

14. The compound of claim 12 wherein
$R_1'$ represents hydroxy;
$R_2$ represents carboxy or esterified carboxy that can be cleaved under physiological conditions;
$R_3'$ represents 1-tetrazolyl; and
n represents an integer from 3 to 8;
or a pharmaceutically acceptable salt thereof.

15. (5R,6S)-2-[4-(tetrazol-1-yl)-but-1-yl]-6-[(1R)-1-hydroxyethyl]-2-penem-3-carboxylic acid or a pharmaceutically acceptable salt thereof according to claim 12.

16. (5R,6S)-2-[5-(tetrazol-1-yl)-pent-1-yl]-6-[(1R)-1-hydroxyethyl]-2-penem-3-carboxylic acid or pharmaceutically acceptable salt thereof according to claim 12.

17. (5R,6S)-2-[7-(tetrazol-1-yl)-hept-1-yl]-6-[(1R)-1-hydroxyethyl]-2-penem-3-carboxylic acid or a pharmaceutically acceptable salt thereof according to claim 12.

18. (5R,6S)-2-[10-(tetrazol-1-yl)-dec-1-yl]-6-[(1R)-1-hydroxyethyl]-2-penem-3-carboxylic acid or a pharmaceutically acceptable salt thereof according to claim 12.

19. (5R,6S)-2-[3-(tetrazol-1-yl)-prop-1-yl]-6-[(1R)-1-hydroxyethyl]-2-penem-3-carboxylic acid or a pharmaceutically acceptable salt thereof according to claim 12.

20. (5R,6S)-2-[3-(tetrazol-1-yl)-prop-1-yl]-6-[(1R)-1-hydroxyethyl] -2-penem-3-carboxylic acid acetoxymethyl ester according to claim 12.

21. (5R,6S)-2-[3-etrazol-1-yl)-prop-1-yl]-6-[(1R)-1-hydroxyethyl]-2-penem-3-carboxylic acid pivaloyloxymethyl ester according to claim 12.

22. A pharmaceutical composition comprising an antibiotically effective amount of a compund of claim 1; or a pharmaceutically acceptable salt thereof; and a pharmaceutically acceptable carrier.

23. A pharmaceutical composition comprising n antibiotically effective amount of a compound of claim 5 wherein
$R_1$ is methyl or ethyl, each substituted by hydroxy; and
$R_2$ is carboxy or physiologically cleavable esterified carboxy;
or a pharmaceutically acceptable salt thereof; and a pharmaceutically acceptable carrier.

24. A pharmaceutical composition comprising an antibiotically effective amount of of a compound of claim 12 wherein,
$R_1'$ is hydroxy; and
$R_2$ is carboxy or physiologically cleavable esterified carboxy;
or a pharmaceutically acceptable salt thereof; and a pharmaceutically acceptable carrier.

25. A method of treating a bacterial infection in a mammal comprising administering to said mammal an antibiotically effective amount of a compound of claim 1 wherein
$R_1$ is methyl or ethyl, each substituted by hydroxy; and
$R_2$ is carboxy or physiologically cleavable esterified carboxy;
or a pharmaceutically acceptable salt thereof.

26. A method of treating a bacterial infection in a mammal comprising administering to said mammal an antibiotically effective amount of a compound of claim 5 wherein R₁ is methyl or ethyl, each substituted by hydroxy; and R₂ is carboxy or physiologically cleavalbe esterified carboxy;

or a pharmaceutically acceptable salt thereof.

27. A method of treating a bacterial infection in a mammal comprising administering to said mammal an antibiotically effective amount of a compound of claim 12;

or a pharmaceutically acceptable salt thereof.

28. (5R,6S)-2-[3-tetrazol-1-yl)-prop-1-yl]-6-[(1R)-1-hydroxyethyl]-2-penem-3-carboxylic acid 1-ethoxycarbonyloxyethyl ester according to claim 12.

29. (5R,6S)-2-[(2R,S)-2-(tetrazol-1-yl)-prop-1-yl]-6-[(1R)-1-hydroxyethyl]-2-penem-3-carboxylic acid or a pharmaceutically acceptable salt thereof according to claim 1.

30. (5R,6S)-2-(tetrazol-1-ylmethyl)-6-(1-hydroxyethyl)-2-penem-3-carboxylic acid or a pharmaceutically acceptable salt thereof according to claim 5.

31. (5R,6S)-2-[2-(tetrazol-1-yl)-ethyl]-6-(1-hydroxyethyl)-2-penem-3-carboxylic acid or a pharmaceutically acceptable salt thereof according to claim 5.

* * * * *